(12) United States Patent
Yuan

(10) Patent No.: US 11,739,302 B2
(45) Date of Patent: Aug. 29, 2023

(54) ENGINEERED VACCINIA VIRUS

(71) Applicant: Shenzhen Hua Yao Kang Ming Biopharmaceutical Co., Ltd., Shenzhen (CN)

(72) Inventor: Ming Yuan, Shenzhen (CN)

(73) Assignee: Shenzhen Hua Yao Kang Ming Biopharmaceutical Co., Ltd., Shenzhen (CN)

( * ) Notice: Subject to any disclaimer, the term of this patent is extended or adjusted under 35 U.S.C. 154(b) by 428 days.

(21) Appl. No.: 16/926,803

(22) Filed: Jul. 13, 2020

(65) Prior Publication Data

US 2021/0009965 A1   Jan. 14, 2021

Related U.S. Application Data

(60) Provisional application No. 62/873,221, filed on Jul. 12, 2019.

(51) Int. Cl.
| | |
|---|---|
| C12N 15/863 | (2006.01) |
| C12N 7/00 | (2006.01) |
| A61K 9/00 | (2006.01) |
| A61K 39/395 | (2006.01) |
| G01N 33/50 | (2006.01) |
| C12Q 1/02 | (2006.01) |
| G01N 33/574 | (2006.01) |
| A61K 31/513 | (2006.01) |
| A61K 31/519 | (2006.01) |
| A61K 31/7068 | (2006.01) |
| A61K 35/768 | (2015.01) |
| A61P 35/00 | (2006.01) |
| A61K 31/505 | (2006.01) |
| A61K 38/20 | (2006.01) |
| A61K 47/00 | (2006.01) |
| A61K 39/00 | (2006.01) |

(52) U.S. Cl.
CPC ............. *C12N 7/00* (2013.01); *A61K 9/0014* (2013.01); *A61K 9/0019* (2013.01); *A61K 9/0043* (2013.01); *A61K 9/0053* (2013.01); *A61K 31/505* (2013.01); *A61K 31/513* (2013.01); *A61K 31/519* (2013.01); *A61K 31/7068* (2013.01); *A61K 35/768* (2013.01); *A61K 38/208* (2013.01); *A61K 38/2013* (2013.01); *A61K 39/3955* (2013.01); *A61K 47/00* (2013.01); *A61P 35/00* (2018.01); *C12Q 1/02* (2013.01); *G01N 33/5005* (2013.01); *G01N 33/57407* (2013.01); *A61K 2039/5252* (2013.01); *C12N 2710/24121* (2013.01); *C12N 2710/24132* (2013.01)

(58) Field of Classification Search
None
See application file for complete search history.

(56) References Cited

U.S. PATENT DOCUMENTS 10,888,594 B2 *   1/2021   Nakao ................ C07K 14/5418
2006/0275794 A1 * 12/2006   Carrino ................ C12Q 1/6876
                                                               435/6.1

FOREIGN PATENT DOCUMENTS

| WO | WO-03103589 A2 * | 12/2003 | ........... A61K 38/193 |
| WO | WO-2015150809 A1 * | 10/2015 | ........... A61K 35/768 |
| WO | WO-2020056424 A1 * | 3/2020 | ........... A61K 31/137 |

OTHER PUBLICATIONS

Huang et al (Molecular Therapy, 2010, 18:264-274).*
De Graaf et al (Cytokine and Growth Factor Reviews, 2018, 41:28-39).*

* cited by examiner

*Primary Examiner* — Laura B Goddard

(57) ABSTRACT

An engineered vaccinia virus, a pharmaceutical composition containing the same, and methods for use in treating a subject in need using the same are provided. The engineered vaccinia virus includes a mutated viral sequence and a heterologous sequence. The mutated viral sequence is used for selective replication in tumor cells and/or activation of immune cells. The heterologous sequence encodes an immune co-stimulatory pathway activating molecule, immunomodulator gene, a truncated viral envelope gene, and/or a tumor suppressor. The heterologous sequence is stably incorporated into the genome of the engineered vaccinia virus. The pharmaceutical composition includes an effective amount of the engineered vaccinia virus and a pharmaceutical acceptable vehicle. The methods for use in treating the subject in need include administering the engineered vaccinia virus to the subject.

18 Claims, 13 Drawing Sheets

Specification includes a Sequence Listing.

FIG. 12A
FIG. 12B
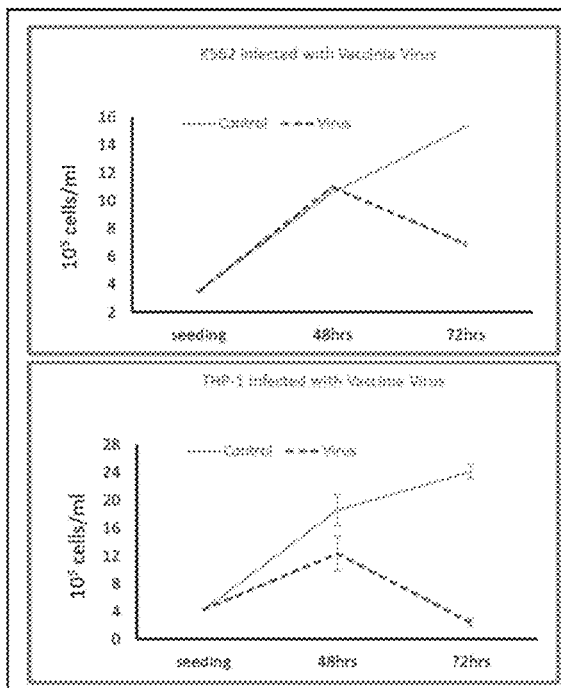
FIG. 12C
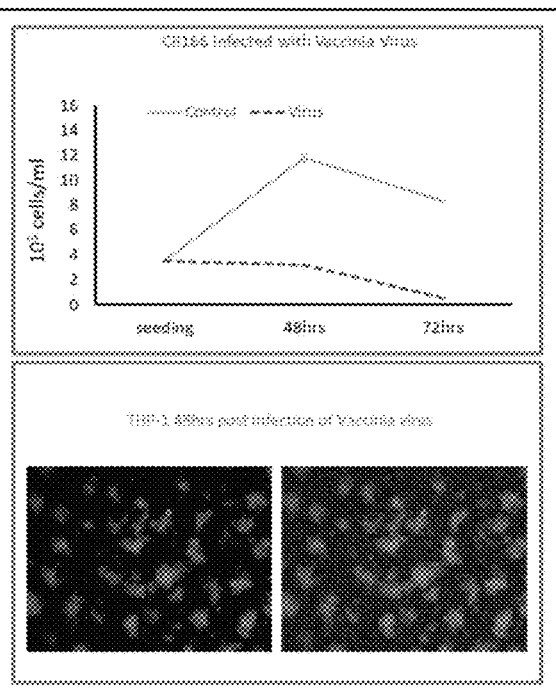
FIG. 12D

ENGINEERED VACCINIA VIRUS

RELATED APPLICATIONS

This application claims the benefit of priority of U.S. Provisional Patent Application No. 62/873,221 filed on Jul. 12, 2019, the contents of which are incorporated herein by reference in their entirety.

SEQUENCE LISTING STATEMENT

The ASCII file, entitled 83665SequenceListing.txt, created on Jul. 12, 2020, comprising 44,614 bytes, submitted concurrently with the filing of this application is incorporated herein by reference.

FIELD AND BACKGROUND OF THE INVENTION

The present disclosure relates to an engineered vaccinia virus for the treatment of cancer.

Cancer is a serious and dangerous disease. There are nearly 5 million new cancer cases in China each year, and the number of patients dying from cancer is close to 3 million. These figures have been increasing year by year. It shows that traditional cancer treatments such as surgery, chemotherapy and radiotherapy are not effective in helping most cancer patients. Therefore, cancer patients are in a great need of more effective treatments. Despite some progress in new cancer immunotherapy, how to treat patients with solid tumor more effectively remains one of the biggest challenges. In recent years, oncolytic viruses, which are one of the types of cancer immunotherapy, have received increasing attention in the industry.

Oncolytic viruses are viruses that target and kill tumor cells by selectively infecting tumor cells or selectively replicating in tumor cells. In addition, oncolytic viruses can effectively provide the risk signals necessary to induce and amplify the host's anti-tumor immune response, thereby allowing the body's immune system to produce a strong and specific anti-tumor immune response.

Vaccinia virus (VV) is a double-stranded DNA virus, its unique properties make it an advantageous option among oncolytic viruses. 1) VV has demonstrated good safety in the process of preventing smallpox as a vaccine against infectious diseases, so its safety as an oncolytic virus can be guaranteed. In addition, it has been further confirmed in many clinical trials that it is safe to use VV as an oncolytic virus. 2) It can rapidly self-replicate in cells, and new virus particles can be produced in about 6-8 hours, so that infected cells can be rapidly lysed. 3) The genome of VV is about 200 Kbp, and this larger genome has a large capacity to carry foreign genes. 4) Vaccinia virus does not require specific receptors to infect cells, therefore it has a wide tropism for different type of tumors. 5) It can be administered in a variety of ways, including topical intratumoral injection, intraperitoneal injection, intrathoracic injection and systemic intravenous injection. This diversity of administering method has made it possible to treat tumors in any part of the body. 6) In addition, the hypoxic microenvironment normally found in solid tumors has a negative effect on the replication and efficacy of many types of oncolytic viruses. However, VV can replicate efficiently in hypoxic environment (Hiley et al, Gene Therapy 17, 281-287). (2010). 7) There are a variety of natural and synthetic promoters that can be applied to VV, which makes it ideal for carrying transgenes. In recent years, clinical results using vaccinia virus have demonstrated that VV has a good anti-tumor effect and is safe (Haddad et al, Annals of Surgical Oncology 19 Suppl 3, S665-674 (2012); Park et al, Lancet Oncol 9: 533-542, (2008); Breitbach et al, Nature 477: 99-102, (2011)).

Various deletion mutants of vaccinia virus have been reported so far. A Western Reserve strain mutant having a thymidine kinase (TK) gene and a viral growth factor (VGF) gene deletion is capable of efficiently eliciting an immune response against a tumor antigen (McCart et al, Cancer Res 61, 8751-8757 (2001)). Furthermore, viruses inserted with a heterologous gene, such as a cytokine encoding gene, can further activate an anti-tumor immune response.

After VV infects tumor cells, VV is released by lysis of infected cells so that the virus can infect tumor cells that are localized or infect tumor cells that are far away from the infected site via circulating blood. The vaccinia virus mainly has two forms of infectious virus particles, namely Intracellular Mature Virus (IMV) and Extracellular Enveloped Virus (EEV) (Appleyard et al., J. Gen. Virology 13, 9-17 (1971)). IMV is a major infectious form of viral particles. EEV is enveloped by the host cell membrane and thus can antagonize host systemic innate (complement) and adaptive (neutralizing antibodies) immune attack, allowing VV to spread widely and over long distances in the host (Smith, G L & Vanderplasschen, A and Law, M J. Gen. Virol. 83, 2915-2931 (2002); Payne, L G & Kristensson, K, J. Gen. Virol. 66 (c), 643-646 (1985)). However, most VV strains produce only a small amount of EEV (only less than 1% of all infectious viruses).

VV has six genes encoding EEV-specific proteins. They are A33R, A34R, A36R, F13L, B5R and A56R. The B5R gene encodes a 42 kDa glycoprotein containing four copies of a 50-70-amino acid repeat, termed a "short consensus repeat" (SCR). Deletion of the B5R gene results in smaller plaques and a significant reduction in EEV formation (<10-fold) (Blasco, R. & Moss, B., J. Virol. 65, 5910-5920 (1991); Engelstad, M. & Smith, G L, Virology 194, 627-637 (1993)). The transmembrane and cytoplasmic tail sequences of B5R are important for targeted packaging of viral proteins (Katz et al, J. Virol. 71, 3178-3187 (1997)). VV carries B5R gene mutants lacking SCR4, SCR3, 4 or SCR 2, 3, 4 produces smaller plaques, but produces infectious EEVs that are dozens of times more than wild-type viruses and form a comet tail plaque distribution (Sanderson et al, J. Gen Virol. 79 (f), 1415-1425 (1998); Mathew et al, J. Virol. 72, 2429-2438 (1998)).

In the past 10 years or so, despite the progress in the field of oncolytic virus research, vaccinia virus-based therapeutic products have not yet entered the clinic, the difficulty is how to scientifically modify the vaccinia virus to have better anti-tumor effect. Therefore, there is an urgent need to develop better oncolytic vaccinia virus products to meet the needs of treating cancer.

There are a variety of vaccinia strains that have varying degrees of virulence to humans and animals. As part of the 1970s smallpox eradication program, many different strains were used around the world. For example, the New York City Department of Health (NYCBOH) strain and its derivatives Wyeth are popular in the United States, while Copenhagen (CPN) and Lister strain are dominant in Europe. Previous study found that Lister strain has a good anti-tumor effect. This project selected Lister strain as an oncolytic virus for development.

SUMMARY OF THE INVENTION

The present disclosure relates to an oncolytic virus, and more particularly to an engineered oncolytic vaccinia virus.

The engineered oncolytic vaccinia virus of the present disclosure is capable of selectively infecting cancer cells, which can be beneficially used in the treatment of cancer.

The present disclosure provides an engineered vaccinia virus comprising a mutated viral sequence and a heterologous sequence, wherein the mutated viral sequence promotes selective replication in tumor cells, and/or activation of immune cells, the heterologous sequence encodes an immune co-stimulatory pathway activating molecule, immunomodulator gene, a truncated viral envelope gene, and/or a tumor suppressor, and the heterologous sequence is stably incorporated into the genome of the engineered vaccinia virus.

In an embodiment of the engineered vaccinia virus, the heterologous sequence is stably incorporated into the mutated viral sequence of the engineered vaccinia virus.

In an embodiment of the engineered vaccinia virus, the mutated viral sequence comprises at least one of:
(a) a mutation(s) in L025, TK, A46R, or any combination thereof;
(b) partially deleted L025, TK, A46R, or any combination thereof;
(c) deleted L025, TK, A46R, or any combination thereof;
(d) a portion or all of the L025, TK, or A46R, which is replaced by one of sequences set forth in SEQ ID NO: 2, 4, 6, 8, 10, 12, or 14;
(e) a portion or all of the L025, TK, or A46R, which is replaced by a tumor targeting gene;
(f) a portion or all of the L025, TK, or A46R, which is replaced by a ligand or an antibody that targets T cells;
(g) a portion or all of the L025, TK, or A46R, which is replaced by a therapeutic gene or a modified version thereof; or
(h) a portion or all of the L025, TK, or A46R is replaced by a therapeutic antibody.

In an embodiment of the engineered vaccinia virus, the heterologous sequence comprises at least one of:
(a) a sequence set forth in SEQ ID NO: 2;
(b) a sequence set forth in SEQ ID NO: 4;
(c) a sequence set forth in SEQ ID NO: 6;
(d) a sequence set forth in SEQ ID NO: 8;
(e) a sequence set forth in SEQ ID NO: 10;
(f) a sequence set forth in SEQ ID NO: 12; or
(g) a sequence set forth in SEQ ID NO: 14.

In an embodiment of the engineered vaccinia virus, the heterologous sequence encodes at least one of:
(a) a sequence set forth in SEQ ID NO: 1;
(b) a sequence set forth in SEQ ID NO: 3;
(c) a sequence set forth in SEQ ID NO: 5;
(d) a sequence set forth in SEQ ID NO: 7;
(e) a sequence set forth in SEQ ID NO: 9;
(f) a sequence set forth in SEQ ID NO: 11; or
(g) a sequence set forth in SEQ ID NO: 13.

In an embodiment of the engineered vaccinia virus, the engineered vaccinia virus comprises a sequence of formula: 5'-A-X-A2-B1-Y—B2-C1-Z—C2-3', wherein A1 and A2 are a left arm and a right arm of a first viral gene respectively, B1 and B2 are a left arm and a right arm of a second viral gene, respectively, C1 and C2 are a left arm and a right arm of a third viral gene, respectively, wherein X, Y, and Z are heterologous genes, each selected from one of immunomodulatory genes, cytokines, therapeutic genes, truncated viral envelope genes, tumor suppressor genes, genes encoding therapeutic antibodies, and genes encoding ligands of the therapeutic antibodies.

In an embodiment of the engineered vaccinia virus, the first viral gene is L025, the second viral gene is TK, and the third viral gene is A46R.

In an embodiment of the engineered vaccinia virus, X is a hybrid gene of IL-21 and modified B5R, Y is 4-1BBL, and Z is HIC1.

In an embodiment of the engineered vaccinia virus, the mutated viral sequence comprises mutations of deletions in L025, TK, and A46R, and the heterologous sequence comprises IL-21 and 4-1BBL.

In an embodiment of the engineered vaccinia virus, the mutated viral sequence comprises mutations of deletions in L025, TK, and A46R, and the heterologous sequence comprises a hybrid gene of IL-21 and modified B5R, and 4-1BBL.

In an embodiment of the engineered vaccinia virus, the immunomodulator genes is a cytokine gene encoding IL-12, IL-21, IL-2, IL-15, IL-8, or a modified version thereof.

In an embodiment of the engineered vaccinia virus, the immune co-stimulatory pathway activating molecule comprises CD40 ligand (CD40L), ICOS ligand, GITR ligand, 4-1BB ligand, OX40 ligand, TL1A, CD30 ligand, CD27, Flt3 ligand, or a modified version thereof.

In an embodiment of the engineered vaccinia virus, the tumor suppressor gene is HIC1.

In an embodiment of the engineered vaccinia virus, the engineered vaccinia virus is selected from the group consisting of Lister, Western Reserve (WR), Copenhagen (Cop), Bern, Paris, Tashkent, Tian Tan, Wyeth (DRYVAX), IHD-J, IHD-W, Brighton, Ankara, CVA382, modified vaccinia ankara (MVA), Dairen I, LC16m8, LC16M0, LIVP, ACAM2000, WR 65-16, Connaught, New York City Board of Health (NYCBH), EM-63 and NYVAC strain.

In an embodiment of the engineered vaccinia virus, the truncated viral envelope gene is B5R containing a short consensus repeats (SCR) 2, SCR3, and SCR4 domains deletion.

In an embodiment of the engineered vaccinia virus, the tumor suppressor is HIC1.

The present disclosure further provides a pharmaceutical composition comprising an effective amount of the engineered vaccinia virus of any one of the embodiments of the present disclosure and a pharmaceutical acceptable carrier.

In an embodiment of the pharmaceutical composition, the pharmaceutical composition is formulated for oral, topical, parenteral delivery, or interventional therapy.

In an embodiment of the pharmaceutical composition, the pharmaceutical composition is formulated for topical intratumoral injection, intraperitoneal injection, intrathoracic injection, systemic intravenous injection, intramuscular injection, subcutaneous injection, intrathecal injections, direct intraventricular injection, intracardiac injection, intranasal injections.

In an embodiment of the pharmaceutical composition, the engineered vaccinia virus is used alone as monotherapy; or in combination with one or more anti-cancer agent, immune suppressors, and/or oncolytic virus enhancers.

In an embodiment of the pharmaceutical composition, the engineered vaccinia virus is used in combination with 5-fluorouracil (FU), folinic acid (FA), methotrexate, capecitabine, oxaliplatin, bevacizumab, cetuximab, immune checkpoint inhibitors (such as anti-PD1, anti-PDL1, anti-CTLA4 agents), other types of oncolytic viruses, pembrolizumab, nivolumab, ipilimumab, atezolizumab, avelumab, adenovirus, or combination thereof.

The present disclosure further provides a method for use in treating a cancer in a subject in need thereof, comprising administering to the subject an effective amount of the engineered vaccinia virus of any one of the embodiments of the present disclosure or the pharmaceutical composition of any one of the embodiments of the present disclosure.

In an embodiment of the method, HIC1 is inactivated, underexpressed, or loss in the cancer.

In an embodiment of the method, the cancer is selected from the group consisting lung cancer, melanoma, pancreatic cancer, liver cancer, colon cancer, breast cancer, glioblastoma, sarcoma, stomach cancer, ovarian cancer, mesothelioma, and leukemia.

A method of increasing tumor-specific infectivity of vaccinia virus, comprising administering the engineered vaccinia virus of any one of the embodiments of the present disclosure to a subject, wherein the engineered vaccinia virus is administered in an amount effective for invoking anti-tumor immune response in a subject.

A method of conferring persistent immunity to tumor relapse in a subject in need thereof comprising administering the engineered vaccinia virus of any one of the embodiments of the present disclosure to the subject.

A method of screening patients based on a percentage of GFP positive cells 48 hours post infection of patient's cancer cells with the engineered vaccinia virus of any one of the embodiments of the present disclosure.

An engineered vaccinia virus for use in inducing cancer cells death, regulating a biological activity of the cancer cells, regulating immune response, enhancing proliferation of T cells, and/or cytotoxicity of T cells, wherein the engineered oncolytic is as provided in any one of the embodiments of the present disclosure.

An engineered vaccinia virus for use in inducing cancer cells death, regulating a biological activity of the cancer cells, regulating immune response, enhancing proliferation of T cells, and/or cytotoxicity of T cells, wherein the biological activity of the cancer cells comprises inhibition of cancer cells replication, inhibition of cancer cells division, inhibition of DNA repair of cancer cells, inhibition of cancer cells migration, or promoting cancer death, wherein the engineered oncolytic is as provided in any one of the embodiments of the present disclosure.

An engineered vaccinia virus for use in the manufacture of a medicament for treating lung cancer, melanoma, pancreatic cancer, liver cancer, colon cancer, breast cancer, glioblastoma, sarcoma, stomach cancer, ovarian cancer, mesothelioma, and leukemia, wherein the engineered oncolytic is as provided in any one of the embodiments of the present disclosure.

An engineered vaccinia virus for use in the manufacture of a medicament for suppressing cancer cells growth, inducing cancer cells death, and/or regulating a biological activity of the cancer cells, wherein the engineered oncolytic is as provided in any one of the embodiments of the present disclosure.

BRIEF DESCRIPTION OF THE SEVERAL VIEWS OF THE DRAWINGS

In order to illustrate a technical solution in the embodiments of the present application or in the prior art more clearly, the accompanying drawings required in the embodiments are introduced briefly hereafter. The accompanying drawings in the following description are merely part of the embodiments of the present application. Based upon the accompanying drawings, people with ordinary skills in the art can obtain other drawings without making inventive efforts.

FIGS. 12A, 12B, 12C and 12D show killing of leukemia cell lines by vaccinia virus. examples of EC50 assay on two cell lines.

DESCRIPTION OF SPECIFIC EMBODIMENTS OF THE INVENTION

Figure 1A:
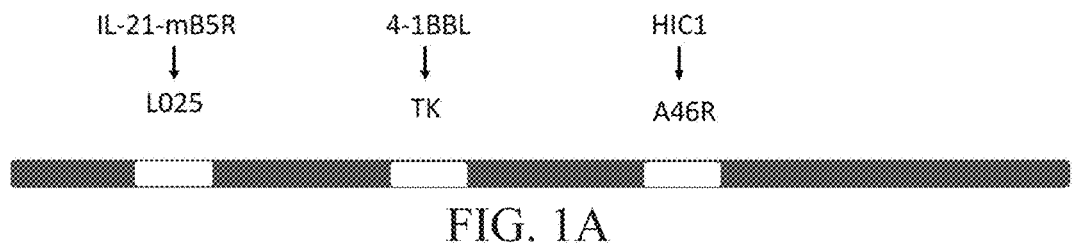
FIG. 1A is a schematic diagram of the product carrying mB5R.

Referring to the drawings in the accompanying drawings, same reference numerals represent same components. The following description is based on the detailed embodiments of the present disclosure as exemplified, and should not be construed as a limitation to other embodiments of the present application which are not described herein in detail.

Figure 1B:
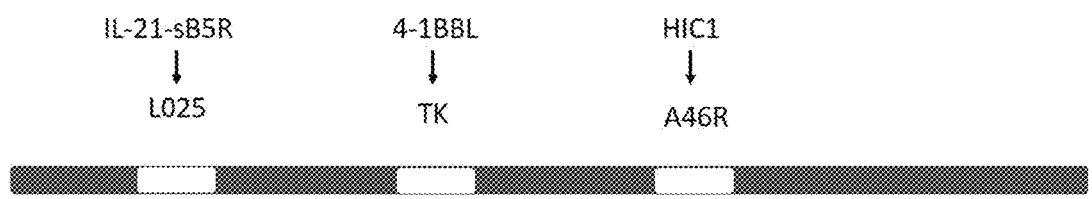
FIG. 1B is a schematic diagram of the product carrying sB5R.

Please refer to FIGS. 1A-1B. FIG. 1A is a schematic diagram of the product carrying mB5R and FIG. 1B is a schematic diagram of the product carrying sB5R.

The vaccinia virus and the viral vector of the present disclosure comprises a sequence of formula: 5'-$A_1$-X-$A_2$-$B_1$—Y—$B_2$—$C_1$—Z—$C_2$-3', wherein $A_1$ and $A_2$ are a left arm and a right arm of a first viral gene respectively, $B_1$ and $B_2$ are a left arm and a right arm of a second viral gene respectively, $C_1$ and $C_2$ are a left arm and a right arm of a third viral gene respectively, wherein X, Y, and Z are each selected from immunomodulatory genes, cytokines, therapeutic genes, and therapeutic antibodies, ligands of the therapeutic antibodies. Exemplary structures of the obtained product are shown in FIGS. 1A and 1B. The first viral gene is L025, the second viral gene is TK, and the third viral gene is A46R. X is a hybrid gene of IL-21 and modified B5R, Y is 4-1BBL, and Z is HIC1.

The gaps between "$A_1$-X-$A_2$" and "$B_1$—Y—$B_2$" and between "$B_1$—Y—$B_2$" and "$C_1$—Z—$C_2$" can contain other viral genes known in vaccinia virus.

Product Design and Construction:

1. TK Gene Deletion and Integration of 4-1BBL Gene into the TK Gene Site

Figure 2A:
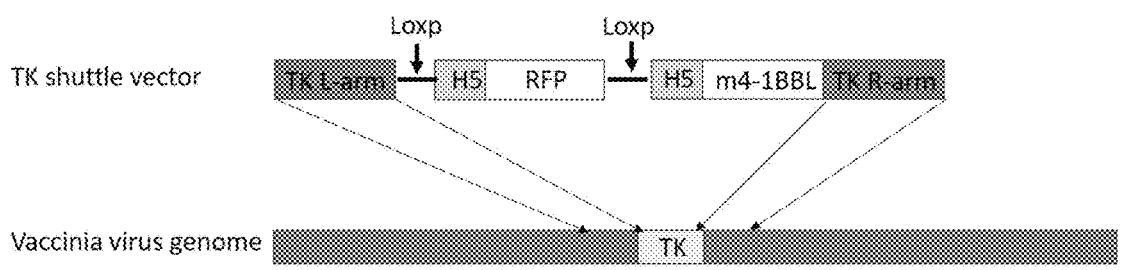
FIG. 2A is a schematic diagram of the shuttle vector carrying mouse 4-1BBL for the deletion of TK gene.
Figure 2B:
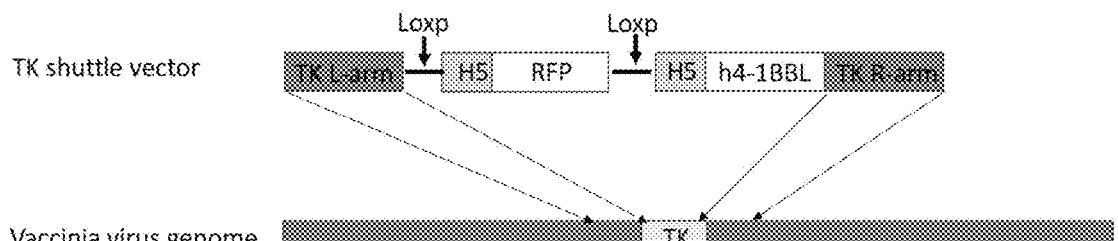
FIG. 2B is a schematic diagram of the shuttle vector carrying human 4-1BBL for the deletion of TK gene.

Please refer to FIGS. 2A-2B. FIG. 2A is a schematic diagram of the shuttle vector carrying mouse 4-1BBL for the deletion of TK gene. FIG. 2B is a schematic diagram of the shuttle vector carrying human 4-1BBL for the deletion of TK gene.

In FIG. 2A, the left arm of the TK targets the left side of the TK gene (L089), and the right arm of the TK targets the right side of the TK gene (L091). The Loxp site is flanked by the H5 promoter and the red fluorescent protein RFP, and is located between the TK left arm and the promoter H5 of the mouse 4-1BBL gene.

In FIG. 2B, the left arm of the TK targets the left side of the TK gene (L089), and the right arm of the TK targets the right side of the TK gene (L091). The Loxp site is flanked by the H5 promoter and the red fluorescent protein RFP, and is located between the TK left arm and the promoter H5 of the human 4-1BBL gene.

The expression cassette is designed as follows (see FIG. 2A and FIG. 2B for a schematic diagram):

TK left arm-loxp-H5-RFP-loxp-H5-m/h4-1BBL-TK right arm

In order to delete two or more genes using the same reporter protein (RFP), it is important to use a suitable homologous recombination system, such as Cre-Lox, or a Flp/FRT system for removal of the reporter gene. The gene insertion elements may be added to the expression cassette around the nucleic acid sequence encoding the protein(s) and upstream of the promoter region driving expression of the protein(s).

The loxp sites are located upstream of H5 and downstream of the RFP, respectively, so that the C5 recombinase can be used to excise the H5-RFP in the new recombinant virus by acting on the FRET site.

The H5 promoter drives expression of the 4-1BBL gene. The amino acid sequence of SPD-m4-1BBL is set forth in SEQ ID NO: 5 and the nucleotide sequence of SPD-m4-1BBL of SPD-m4-1BBL is set forth in SEQ ID NO: 6. The amino acid sequence of SPD-h4-1BBL is set forth in SEQ ID NO: 7 and the nucleotide sequence of SPD-h4-1BBL of SPD-h4-1BBL is set forth in SEQ ID NO: 8.

In order to perform targeted homologous recombination at the TK gene (L090) site of vaccinia virus, it is necessary to provide an additional sequence complementary to the TK gene and/or the gene adjacent to the TK gene for the recombinant region used to produce the vector of the present disclosure. A TK left arm (L-arm) was provided to target the left side of the TK gene (L089) and the right arm of the TK (R-arm) to target the right side of the TK gene (L091). Then, the actual expression cassette comprising 4-1BBL gene and the reporter gene RFP can be located between the TK-L arm and the TK-R arm, and they can be inserted into the targeted TK region of the vaccinia virus. The expression cassette can be inserted into the recombinant vector prior to transformation of the vaccinia virus vector.

2. Deletion of L025 Gene and Integration of Interleukin 21 (IL-21) and mB5R (or sB5R) into the L025 Region Please refer to FIG. 3A-3B. FIG. 3A shows the shuttle vector carrying mouse IL-21 and modified B5R (mB5R/sB5R) for deletion of the L025 gene. FIG. 3B shows the shuttle vector carrying human IL-21 and modified B5R (mB5R/sB5R) for deletion of the L025 gene.

In FIG. 3A, the left arm of L025 targets the left side of the L025 gene (L024), and the right arm of L025 targets the right side of the L025 gene (L026). The FRT site is located on both sides of the H5 promoter and the red fluorescent protein RFP, and is located between the left arm of L025 and the right arm of L025.

In FIG. 3B, the left arm of L025 targets the left side of the L025 gene (L024), and the right arm of L025 targets the right side of the L025 gene (L026). The FRT site is located on both sides of the H5 promoter and the red fluorescent protein RFP, and is located between the left arm of L025 and the right arm of L025.

The expression cassette is designed as follows (see FIGS. 3A and 3B for a schematic diagram):

L025 left arm-FRT-H5-RFP-FRT-H5-m/sB5R-H5-m/hIL-21-L025 right arm

Red fluorescent protein (RFP) is used as a reporter protein to facilitate the screening of new recombinant viruses. A promoter is provided upstream of the reporter protein to drive expression of the reporter protein, here using the H5 promoter. The FRT are recognition site for Flipase, so that the RFP can be excised.

The amino acid sequence of mouse IL-21 is set forth in SEQ ID NO: 9 and the nucleotide sequence of mouse IL-21 is set forth in SEQ ID NO: 10. The amino acid sequence of human IL-21 is set forth in SEQ ID NO: 11 and the nucleotide sequence of human IL-21 is set forth in SEQ ID NO: 12.

Please refer to FIG. 5. FIG. 5 shows structure diagrams of the mB5R/sB5R gene. mB5R consists of a signal peptide, stalk, a transmembrane region (TM) and an intracellular tail segment (CT) gene fragment. sB5R consists of a signal peptide, short consensus repeat 1 (SCR1), stalk, a transmembrane region (TM) and an intracellular tail segment (CT) gene fragment.

The H5 promoter drives the expression of the immunotherapeutic gene IL21 and the expression of mB5R or sB5R. See FIG. 5 for schematic structure diagrams of mB5R and sB5R. The amino acid sequence of mB5R is set forth in SEQ ID NO: 1 and the nucleotide sequence of mB5R is set forth in SEQ ID NO: 2. The amino acid sequence of sB5R is set forth in SEQ ID NO: 3 and the nucleotide sequence of sB5R is set forth in SEQ ID NO: 4.

The above recombinant region needs to be inserted into the L025 gene of vaccinia virus. Here, insertion was performed using a method of homologous recombination, and the integration site was between the left and right arms of L025.

In order to perform targeted homologous recombination at the L025 gene site of vaccinia virus, it is necessary to provide an additional sequence complementary to the L025 gene and/or the gene adjacent to the L025 gene for the recombinant region used to produce the vector of the present disclosure. The L025 left arm (L-arm) was provided to target the left side of the L025 gene (L024) and the right arm of the L025 (R-arm) to target the right side of the L025 gene (L026). The actual expression cassette comprising the HIC1 gene and the reporter gene GFP can then be placed between the L025-L arm and the L025-R arm, and they can be inserted into the targeted L025 region of the vaccinia virus. The expression cassette can be inserted into the recombinant vector prior to transformation of the vaccinia virus vector.

3. The HIC1 Gene is Inserted into the A46R Region.

Figure 4:
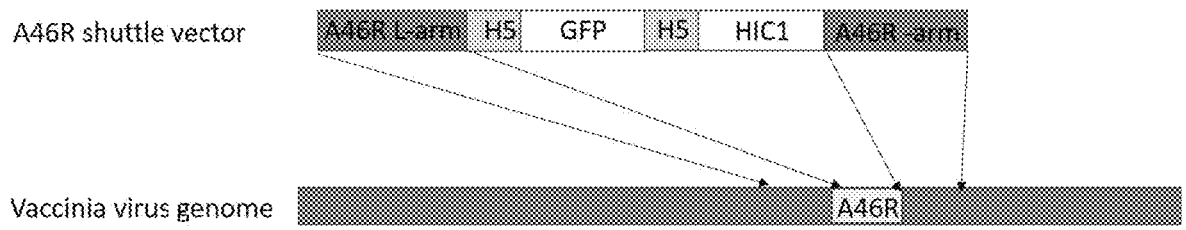
FIG. 4 shows the shuttle vector carrying the HIC1 gene for deleting the A46R gene.
Figure 5:
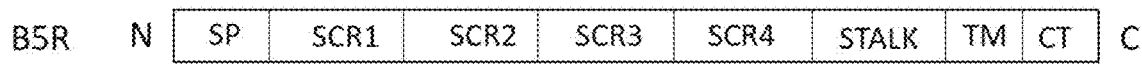
FIG. 5 shows structure diagrams of the mB5R/sB5R gene.
Figure 5:
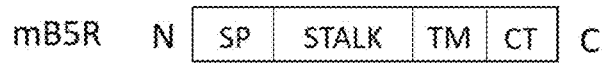
Figure 5:
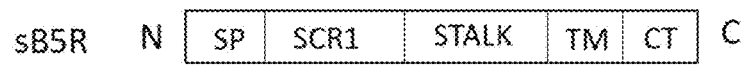

Please refer to FIG. 4. FIG. 4 shows the shuttle vector carrying the HIC1 gene for deleting the A46R gene. The left arm of A46R targets the left side of the A46R gene (L163), and the right arm of A46R targets the right side of the A46R gene (L165). The H5 promoter drives the expression of green fluorescent protein GFP. The H5 promoter drives expression of the HIC1 gene.

The expression cassette is designed as follows (see FIG. 4 for a schematic diagram):

A46R left arm-H5-GFP-H5-HIC1-A46R right arm

In order to perform targeted homologous recombination at the A46R gene (L164) site of vaccinia virus, it is necessary to provide an additional sequence complementary to the A46R gene and/or the gene adjacent to the A46R gene for the recombinant region used to produce the vector of the present disclosure. The A46R left arm (L-arm) was provided to target the left side of the A46R gene (L163) and the right arm of the A46R (R-arm) to target the right side of the A46R gene (L165). The actual expression cassette comprising the HIC1 gene and the reporter gene GFP can then be placed between the A46R-L arm and the A46R-R arm, and they can be inserted into the targeted A46R region of the vaccinia virus. The expression cassette can be inserted into the recombinant vector prior to transformation of the vaccinia virus vector.

Materials and Methods

Cell lines: All tumor cell lines used were from the ATCC. All human cancer cell lines were genotyped by STR assay. The murine tumor cell lines used in this study included: the colorectal cancer cell line MC38 was derived from C57B/6 mice. CV1 is an African green monkey "normal" kidney cell line obtained from ATCC, Virginia, USA, and is used as a stock cell line to facilitate large-scale production of the virus as well as all virus titration assays.

Virus: The wild type VV Lister is commercially available from American type culture collection (ATCC) under ATCC accession number VR-1549™. The wild type VV Lister is also deposited at China Center for Type Culture Collection (CCTCC) under CCTCC deposition number: V201937. The date of deposit is Jul. 4, 2019. The strain designation is Lister vaccinia virus 01(VV01). Detailed information can also be obtained from the product sheet of ATCC VR-1549™. The engineered VV Lister is deposited at CCTCC under CCTCC deposition number: V201938. The date of deposit is Jul. 4, 2019. The strain designation is Vaccinia virus Lister strain KM1. Both the wild type VV Lister and the engineered VV Lister are deposited pursuant to the Budapest Treaty. The wild type VV Lister and the engineered VV Lister are deposited at China Center for Type Culture Collection (CCTCC), College of Life Sciences, Wuhan University Wuhan 430072, China. The depositor of the wild type VV Lister and the engineered VV Lister is Shenzhen Hua Yao Kang Ming Biopharmaceutial Co., Ltd., 14 Jinhui road, Pingshan District, Shenzhen, China (the Applicant).

Construction of the TK Shuttle Vector:

The TK shuttle vector includes the left side of the TK gene targeting the TK gene (L089) and the right arm of the TK targeting the right side of the TK gene (L091). The Loxp site is flanked by the H5 promoter and the red fluorescent protein RFP and is located between the TK left arm and the promoter H5 of the 4-1BBL gene. All of the above sequences were put together by us, and synthesized by a company and cloned into the PUC57 vector.

Figure 3A:
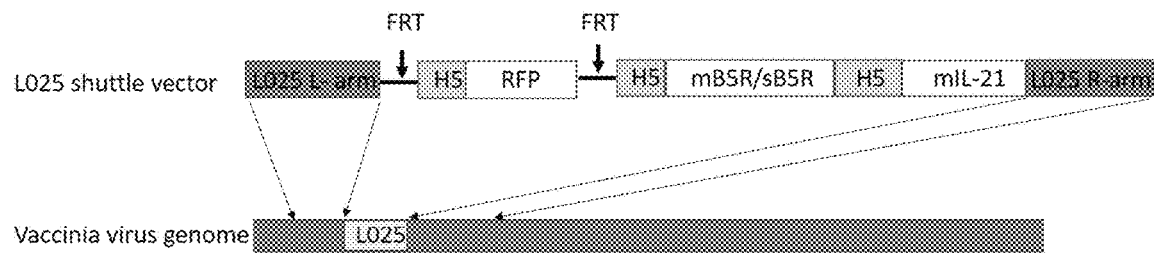
FIG. 3A shows the shuttle vector carrying mouse IL-21 and modified B5R (mB5R/sB5R) for deletion of the L025 gene.
Figure 3B:
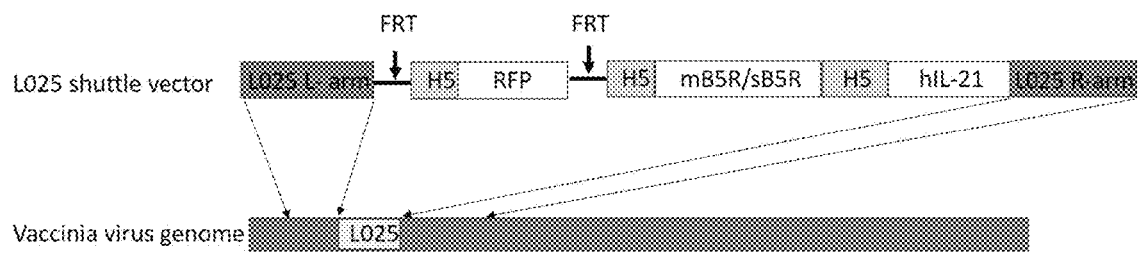
FIG. 3B shows the shuttle vector carrying human IL-21 and modified B5R (mB5R/sB5R) for deletion of the L025 gene.

Construction of the L025 Shuttle Vector:

The schematic structure diagram of the L025 shuttle vector is shown in FIGS. 3A and 3B. The L025 shuttle vector includes the L025 left arm targeting the left side of the L025 gene (L024) and the L025 right arm targeting the right side of the L025 gene (L026). The FRT site is located on both sides of the H5 promoter and the red fluorescent protein RFP and is located between the left arm of L025 and the promoter H5 of the mB5R/sB5R gene. All of the above sequences were spliced together and synthesized by the company and cloned into the PUC57 vector.

Construction of the A46R Shuttle Vector:

The schematic structure diagram of the A46R shuttle vector is shown in FIG. 4. The A46R shuttle vector includes the A46R left arm targeting the left side of the A46R gene (L163) and the A46R right arm targeting the right side of the A46R gene (L165). The H5 promoter drives the expression of green fluorescent protein GFP. The H5 promoter drives expression of the HIC1 gene. All of the above sequences were put together by us, and synthesized by a company and cloned into the PUC57 vector.

Obtain the mB5R Gene:

mB5R consists of the signal peptide, stalk, transmembrane (TM) and intracellular tail (CT) gene segments. The H5 promoter drives expression of the sB5R gene.

Obtaining the sB5R Gene:

sB5R consists of the signal peptide, SCR1, stalk, transmembrane (TM) and intracellular tail (CT) gene segments.

Cas9-Mediated Homologous Recombination:

$3 \times 10^5$ CV-1 cells were seeded into one well of a six-well plate one day prior to transfection. A gRNA vector (L25gRNA targeting the L025 region, TKgRNA targeting the TK region, A46RgRNA targeting the A46R region) was co-transfected with Cas9 into CV-1 cells in a six-well plate. The next day, the well transfected with the gRNA vector and the Cas9 gene was infected with 0.01 PFU/cell backbone virus. The shuttle vector for homologous recombination was transfected into the infected wells 2 hours after virus infection. Cells were harvested after 24 hours and frozen at −80° C. for recombinant virus purification.

Purification of Recombinant Virus:

Cell lysates collected from Cas9-mediated homologous recombination were thawed, and 0.5 µl of this lysate was used to infect all 6 wells of a six-well plate containing CV1 cells grown to 80-90% confluence. After 48 hours of infection, each well was examined under a fluorescence microscope for viruses that emitted red or green fluorescence. After identifying positive infection spots, mark them on the lower surface of the plate with a marker. The plaques were then carefully selected with a 20 µl tip after aspirating the medium from the wells in a fume hood for culturing the cells. The tip was then immersed in a cryotube containing 200 microliters of cell culture fluid. After one freeze-thaw cycle, 5-20 µl of this virus solution was added to each well of a new 6-well plate containing CV1 cells. This process is repeated until each plaque expresses red or green fluorescence, i.e., all plaques are formed by recombinant virus. Typically, 3 to 5 rounds of plaque purification are required to obtain a pure recombinant virus. After confirming that the virus has been purified, the infected cells are scraped off and centrifuged to obtain a cell pellet. Then some cells are taken to extract viral DNA. The purity of the virus was confirmed by PCR amplification of the target gene from the extracted viral DNA.

Amplification of the Virus:

Once the recombinant virus was confirmed to be the desired recombinant virus, 50 µl of the virus lysate was added to a T175 flask containing CV1 cells, and grown to 80-90% confluence in a cell culture medium containing about 30 ml. After 48 hours, the cells and medium were scraped off and "primary virus amplification" was saved.

Verify the Recombinant Virus that Deleted the L025 Gene:

CV-1 cells were infected with the purified virus. Infected cells were harvested 2 days after infection, and the VV DNA was extracted. To verify the deletion of the L025 gene, a DNA fragment spanning the L025 gene and the L026 gene was amplified by PCR using a forward primer (SEQ ID NO: 15: 5'-TATCTAGCAATGGACCGT-3') (within the L025 gene) and a reverse primer (SEQ ID NO: 16: 5'-CCGAAGGTAGTAGCATGGA-3') (within the L026 gene). Amplification of the control gene A DNA fragment spanning the A46R and A47L genes was obtained by PCR amplification using a forward primer (SEQ ID NO: 17: 5'-TTGGCTATTAAACAGTATGGA-3') and a reverse primer (SEQ ID NO: 18: 5'-GGATCCCGATAACAAATG-3'). The PCR product was analyzed by 1% agarose gel electrophoresis.

Verify the Recombinant Virus that Expresses mB5R or sB5R Gene:

To verify the incorporation of mB5R gene in the recombinant virus, mB5R was amplified by PCR using a forward primer (SEQ ID NO: 19: 5'-ATGAAAACGAT-TTCCGTTGTTACGT-3') and a reverse primer (SEQ ID NO: 20: 5'-TCACGGT AGCAATTTATGGAACTT-3').

To verify the incorporation of sB5R gene in the recombinant virus, sB5R gene was amplified by PCR using a forward primer (SEQ ID NO: 21: 5'-ATGAAAACGAT-TTCCGTTGTTACGT-3') and a reverse primer (SEQ ID NO: 22: 5'-TCACGGTAGCAATTTATGGAACTT-3').

Excision of RFP Using Flp Recombinase:

pCAG-Flpe (from Addgene) was transfected into one well of a six-well plate in CV-1 cells. CV-1 cells were infected with 100-200 recombinant viruses Flp-RFP VV 24 hours after transfection with pCAG-Flpe. Two days later, RFP-negative plaques were picked and used to infect CV-1 cells in six-well plates to purify RFP-negative plaques. RFP-negative plaques were then picked and infected with CV-1 cells until no RFP-positive plaques were observed under fluorescent microscope every 2 days.

Verify the Recombinant Virus that Deleted the TK Gene:

CV-1 cells were infected with the purified virus. Infected cells were harvested 2 days after infection, and the VV DNA was extracted. To verify the deletion of the TK gene, use the forward primer (SEQ ID NO: 23: 5'-GT-TATAGTAGCCGCACTCGA-3') (within the TK gene) and the reverse primer (SEQ ID NO: 24: 5'-ATTTCAGCT-GAATATGAAGGA-3') (within the L091 gene) for PCR amplification. A DNA fragment spanning the TK gene and the L091 gene. Amplification of the control gene A DNA fragment spanning the A46R and A47L genes was obtained by PCR amplification using a forward primer (SEQ ID NO: 17: 5'-TTGGCTATTAAACAGTATGGA-3') and a reverse primer (SEQ ID NO: 18: 5'-GGATCCCGATAACAAATG-3'). The PCR product was analyzed by 1% agarose gel electrophoresis. The PD1 antibody gene was confirmed by PCR amplification of its gene fragment. The primers used were: (SEQ ID NO: 25: 5'-TCATAAATACCCGAGC-CACC-3') and (SEQ ID NO: 26: 5'-ACCCATTCAA-GACCCTTTCC-3').

Excision of RFP Using Cre Recombinase:

pCAG-Cre (from Addgene) was transfected into CV-1 cells in one well of a six-well plate. CV-1 cells were infected with 100-200 Cre-RFP viruses 24 hours after transfection with pCAG-Cre. Two days later, RFP-negative plaques were selected and used to infect CV-1 cells in six-well plates to purify RFP-negative plaques. RFP-negative plaques were then picked and infected with CV-1 cells until no RFP-positive plaques were observed under fluorescent microscope every 2 days.

Verify the Recombinant Virus that Deleted the A46R Gene:

CV-1 cells were infected with the purified virus. Infected cells were harvested 2 days after infection, and the VV DNA was extracted. To verify the deletion of the A46R gene, use the forward primer (SEQ ID NO: 17: 5'-TTGGCTAT-TAAACAGTATGGA-3') (within the A46R gene) and the reverse primer (SEQ ID NO: 18: 5'-GGATCCCGA-TAACAAATG-3') (within the A47R gene) for PCR amplification. A DNA fragment spanning the A46R gene and the A47R gene. The control gene was amplified by PCR using a forward primer (SEQ ID NO: 27: 5'-TGTTGTTCGCTGC-TATGA-3') and a reverse primer (SEQ ID NO: 28: 5'-TGGCACAACCATATCTTGTA-3') to amplify a DNA fragment of the L09 gene. The PCR product was analyzed by 1% agarose gel electrophoresis. Detection of HIC1 expression was confirmed by western blotting by obtaining proteins extracted from cells infected with the recombinant virus.

Enzyme-Linked Immunosorbent Assay:

Expression of mIL-21 and hIL-21 was detected by enzyme-linked immunosorbent assay ELISA according to the reagent manufacturer's instructions.

Large-Scale Virus Production:

The primary virus amplification from above was rapidly frozen and thawed once and diluted to the volume required for cell culture required to infect 36 T175 flasks (80-90% confluence) containing CV1 cells. After 48 hours, infected CV1 cells were harvested by scraping and collected by repeating centrifugation at 2,000 rpm (4° C.) for several rounds. The precipitate was washed in PBS, resuspended in 12 ml of 10 mM Tris-HCl (pH 9) buffer and stored at −80° C. for later purification.

Virus Purification:

The concentrated viral lysate suspension from above was thawed once and vortexed for a few seconds. After centrifugation at 2,000 rpm for 5 minutes at 4° C., the supernatant (containing released virions) was collected and diluted to a total volume of 30 ml with 10 mM Tris-HCl buffer. A 30 ml average was placed in four Beckman ultracentrifuge tubes, followed by gently adding 17 ml of 36% sucrose solution to the virus solution and centrifuging at 13,500 rpm for 80 minutes at 4° C. The final pellet was resuspended in 1-4 ml of virus resuspension buffer (PBS; 10% glycerol; 138 mM NaCl; pH 7.4). And save at −80° C.

Determination of Viral Replication:

Depending on the growth rate, cells were seeded at 2 to $4 \times 10^5$ cells per well in 3 wells of a 6-well plate containing cell culture medium, and infected with 1 PFU/cell of vaccinia virus the next day. Infected cells and their culture solutions were collected at 24 hours, 48 hours, and 72 hours after infection, respectively. The virus concentration is then determined.

Evaluation of Viral Cytotoxicity In Vitro:

Cells were seeded at $1 \times 10^3$ and $1 \times 10^4$ cells/well in 96-well plates according to growth rate and infected with virus after 16-18 hours. Cell viability at day 6 after viral infection was determined by MTS assay and EC50 values were calculated as previously described (viral dose killed 50% of tumor cells), all assays were performed at least three times.

Evaluation of Solid Tumor Cells Sensitivity to the Viral Infection In Vitro:

Cells were seeded at $3\times10^5$ cells/well in 6-well plates according to growth rate and infected with virus after 16-18 hours. Cell viability at day 2 after viral infection was determined by crystal violet staining and results were scanned as previously described.

Evaluation of Leukemia Cell Lines Sensitivity to the Viral Infection In Vitro:

Cells were seeded at $3\times10^5$ cells/well in 6-well plates in triplicate according to growth rate and infected with virus after cell seeding. Cell viability at day 1,2 and 3 after viral infection was determined by cell counting with trypan blue staining to differentiate live and dead cells.

Evaluation of Leukemia Patient's Sample's Sensitivity to the Viral Infection in Vitro:

Five milliliters blood was drawn into an anticoagulation tube from leukemia patient with consent. Blood sample was span at 2000 rpm for 5 minutes, the plasma was removed and 5 milliliters red cell lysis buffer were added into the tube, then was incubated at room temperature for 10 minutes. After lysis of red cells, sample was transferred into a 15 ml tube containing 8 mls sterile PBS, and span at 2000 rpm for 5 minutes. Supernatant was removed after centrifugation, and 5 mls RPMI 1640 containing 10% FBS and antibiotics were used to resuspend the cell pellet. Cells were seeded at $1\times10^6$ cells/well in 24-well plates for two wells and one well was infected with 1 pfu KM1 virus/cell after cell seeding, the other well was used as control. Three days after virus infection, infected cells were observed and photographed under fluorescence microscope, then infected cells and control cells were collected into 15 ml tubes containing 10 mls of PBS and span at 2000 rpm for 5 minutes. 100 uls of antibodies mixture containing L/D, CD14, CD16 and CD33 antibodies in PBS were added into the cell pellet and stain the cells for 15 minutes in dark at room temperature. The stained cells were washed once with PBS after staining, and resuspend the cells in 300 uls of PBS, then analyzed on FACs.

In Vivo Efficacy Experiments for Treatment of Cancer Using KM1.

By subcutaneously injecting $5\times10^6$ cancer cells, a subcutaneous tumor of the back was established in 10 mice per treatment group and the diameter was 0.4-0.5 cm, and then the mice were regrouped by tumor size and received $1\times10^8$ PFU (immune-competent mice) or PBS on days 1, 2, 3, 4, and 5 days. Tumor volume (volume=(length×width $2\times\pi$)/6) was measured twice a week until the mice were sacrificed when the tumor area reached 1.69 cm2. The animals used were 4-5 week male Syrian hamsters.

Statistical Analysis:

Comparative statistical analysis was performed using Graphpad Prism 5 unless otherwise stated. Dual condition comparisons were performed using unpaired t-tests. For additional variables of more than one condition, 1 or 2 ANOVA is performed separately. Survival data is represented as a Kaplan-Meier plot with log-rank analysis to plot whether any differences between the groups have statistically significant differences.

An oncolytic vaccinia virus and a viral vector thereof are provided and comprises one or more of the following features:

(a) Generating deletion of a combination of viral genes and introduces immunoregulatory genes (e.g. IL21 and 4-1BBL), a tumor suppressor gene (e.g. HIC1), and a novel viral spread gene mB5R/sB5R into infected target cells.

(b) Deletion of TK gene allows the vaccinia virus to be targeted for replication in tumor cells. The thymidine kinase (TK) of vaccinia virus allows quiescent cells (such as the vast majority of normal cells in the body) to produce thymidine for replication. The TK-deficient vaccinia virus is dependent on the thymidine kinase produced by the host cell. Thymidine kinase is naturally produced in tumor cells but not produced or produced in low quantity in normal cells. Therefore, TK-deficient vaccinia virus can selectively replicate in tumor cells, especially tumor cells with activated EGFR/Ras/ERK pathway.

(c) Deletion of L025 gene. The protein encoded by the L025 gene can suppress the immune response by inhibiting the activation of the NF Kappa B signaling pathway in immune cells. Deletion of the L025 gene can abolish the immune system's inhibition of the gene product, which can improve the anti-tumor immune response.

(d) Deletion of A46R gene. The protein encoded by the A46R gene inhibits the activation of immune cells by acting upstream of the NF Kappa B signaling pathway. Deletion of this gene helps to improve the anti-tumor immune response.

(e) The virus carries additional B5R-partial-region-deletion gene (mB5R or sB5R) for vaccinia virus.

(f) The virus carries interleukin 21 (IL-21) gene. Interleukin 21 also activates NK and killer T cells. The virus carrying interleukin 21 facilitates to enhance immune response against tumor. The therapeutic gene is inserted into the L025 region.

(g) The virus carries 4-1BBL gene. 4-1BB is expressed on the activated T cells, 4-1BB binding to its ligand 4-1BBL enhances the proliferation and cytotoxicity of T cells. To make this product more effective, 4-1BBL gene is incorporated into the virus. The therapeutic gene is inserted into the TK region.

(h) The virus carries a tumor suppressor gene HIC1 gene. HIC1 is inactivated or lost in many tumors. In vivo experiments have shown that expression of this gene in tumors that have lost the gene can inhibit tumor progression. This gene is inserted into the A46R gene region.

(i) The virus carries interleukin 12 (IL-12) gene. Interleukin 12 is known to regulate and activate natural killer cells (NK cells) and killer T cells. The interleukin 12 carried by this product has shown activating NK and T cells in a preliminary efficacy experiment. The therapeutic gene is inserted into the A46R region.

(j) Provide new strategies for deleting multiple viral genes. In the process of constructing the virus, the inventors are the first to introduce the CRISPR Cas9 system to delete the fluorescent protein for gene screening. The various gRNA sequence designed for CRISPR Cas9 system can be used to repeatedly delete the fluorescent protein, so that the vaccinia virus with any combination of genes can be deleted.

According to the feature (e) of the present disclosure, a vaccinia virus vector comprising a nucleic acid sequence encoding a domain deleted B5R gene is provided. This sequence was integrated into and replaced the L025 gene of vaccinia virus. This product carries mB5R/sB5R to allow the virus to spread better, thereby increasing its ability to kill tumor cells.

The B5R gene of vaccinia virus has an open reading frame (ORF) that encodes a membrane protein essential for the formation of EEV. Deletion of the B5R ORF results in a significant decrease in the production of EEV, and therefore, the virus produces small cell-infected plaques in vitro and the ability to spread in vivo is severely degraded. The extracellular portion of B5R consists primarily of four domains that are similar to the short consensus repeats (SCR) present in complement regulatory proteins.

The above partial mB5R gene or sB5R can be driven to be expressed by its upstream promoter. Thus, the nucleic acid sequence of the promoter can be part of an expression cassette. The expression cassette can be part of a vector comprising a promoter, an open reading frame (and a 3' untranslated region). A promoter is a region of DNA with a specific sequence that initiates transcription of its downstream genes. Promoters for expressing heterologous genes in vaccinia include promoters that control early and late transcriptional activities, such as mH5, H5, P7.5 and pE/L. A heterologous gene is a gene that is not normally found in a virus.

An embodiment of the present disclosure provides a sequence, comprising at least one of:
(a) a sequence set forth in SEQ ID NO: 1;
(b) a sequence set forth in SEQ ID NO: 3;
(c) a sequence set forth in SEQ ID NO: 5;
(d) a sequence set forth in SEQ ID NO: 7;
(e) a sequence set forth in SEQ ID NO: 9;
(f) a sequence set forth in SEQ ID NO: 11;
(g) a sequence set forth in SEQ ID NO: 13;
(h) therapeutic gene or a modified version thereof;
(i) 4-1BBL gene or a modified version thereof; or
(j) ligands or antibodies that target T cells.

An embodiment of the present disclosure provides a virus, comprising at least one of:
(a) a sequence set forth in SEQ ID NO: 1;
(b) a sequence set forth in SEQ ID NO: 3;
(c) a sequence set forth in SEQ ID NO: 5;
(d) a sequence set forth in SEQ ID NO: 7;
(e) a sequence set forth in SEQ ID NO: 9;
(f) a sequence set forth in SEQ ID NO: 11;
(g) a sequence set forth in SEQ ID NO: 13;
(h) therapeutic gene or a modified version thereof;
(i) 4-1BBL gene or a modified version thereof; or
(j) ligands or antibodies that target T cells.

The sequence may further comprise therapeutic genes including immunomodulators, immune co-stimulatory pathway activating molecules, checkpoint inhibitors, cytotoxic genes, tumor suppressor genes, anti-angiogenesis genes, etc.

The immunomodulator genes may include cytokine genes. Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and —II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10 IL-11, IL-12; IL-13, IL-14, IL-15, IL-16, IL-17, IL-18, IL-19, IL-20, IL-24, LIF, G-CSF, GM-CSF, M-CSF, EPO, kit-ligand or FLT-3. Most preferably, IL-12, IL-21, IL-2, IL-15, IL-8 or a modified version of any of these.

The immune co-stimulatory pathway activating molecules may include gene encodes CD40 ligand (CD40L), ICOS ligand, GITR ligand, 4-BB ligand, OX40 ligand, TLA, CD30 ligand, CD27 or Flt3 ligand or a modified version of any of these The checkpoint inhibitors may include PD-1 inhibitor, PD-L1 inhibitor, CTLA-4 inhibitor or a modified version of any of these.

The tumor suppressor genes may include HIC1, etc. or a modified version of any of these.

An embodiment of the present disclosure provides a sequence, comprising at least one of:
(a) a mutation(s) in L025, TK, A46R, or any combination thereof;
(b) partially deleted L025, TK, A46R, or any combination thereof;
(c) deleted L025, TK, A46R, or any combination thereof;
(d) a portion or all of the L025, TK, or A46R is replaced by one of sequences set forth in SEQ ID NO: 1-2;
(e) a portion or all of the L025, TK, or A46R is replaced by one of sequences set forth in SEQ ID NO: 3-4;
(f) a portion or all of the L025, TK, or A46R is replaced by 4-1BBL or a modified version thereof;
(g) a portion or all of the L025, TK, or A46R is replaced by HIC1 or a modified version thereof;
(h) a portion or all of the L025, TK, or A46R is replaced by a tumor targeting gene;
(i) a portion or all of the L025, TK, or A46R is replaced by a ligand or an antibody that targets T cells;
(j) a portion or all of the L025, TK, or A46R is replaced by a therapeutic gene or a modified version thereof; and
(k) a portion or all of the L025, TK, or A46R is replaced by a therapeutic antibody.

An embodiment of the present disclosure provides a virus, comprising at least one of:
(a) L025, TK, or A46R mutation;
(b) partially deleted L025, TK, or A46R;
(c) deleted L025, TK, or A46R;
(d) a portion or all of the L025, TK, or A46R is replaced by one of sequences set forth in SEQ ID NO: 1-2;
(e) a portion or all of the L025, TK, or A46R is replaced by one of sequences set forth in SEQ ID NO: 3-4;
(f) a portion or all of the L025, TK, or A46R is replaced by 4-1BBL or a modified version thereof;
(g) a portion or all of the L025, TK, or A46R is replaced by HIC1 or a modified version thereof;
(h) a portion or all of the L025, TK, or A46R is replaced by a tumor targeting gene;
(i) a portion or all of the L025, TK, or A46R is replaced by a ligand or an antibody that targets T cells;
(j) a portion or all of the L025, TK, or A46R is replaced by a therapeutic gene or a modified version thereof; and
(k) a portion or all of the L025, TK, or A46R is replaced by a therapeutic antibody.

An embodiment of the present disclosure provides an expression vector or a host cell comprising any sequence described here above.

An embodiment of the present disclosure provides a virus used for a method of treating the human or animal body, comprising at least one of:
(a) used alone as monotherapy; and
(b) used in combination with one or more anti-cancer agent.

An embodiment of the present disclosure provides a virus used for use in the manufacture of a medicament for treating the human or animal body.

An embodiment of the present disclosure provides a virus used for use in inducing cancer cells death, regulating a biological activity of the cancer cells, regulating immune response, enhancing proliferation and/or cytotoxicity of T cells.

An embodiment of the present disclosure provides a virus used for use in the manufacture of a medicament for suppressing cancer cells growth, inducing cancer cells death, and/or regulating a biological activity of the cancer cells.

The biological activity of the cancer cells comprises inhibition of cancer cells replication, inhibition of cancer cells division, inhibition of DNA repair of cancer cells, inhibition of cancer cells migration, or promoting cancer death.

An embodiment of the present disclosure provides a product of manufacture comprising a virus in a sterile vial, ampoule, or syringe.

An embodiment of the present disclosure provides a pharmaceutical composition comprising a virus of the embodiments of the present disclosure.

In an embodiment of the present disclosure, the pharmaceutical composition further comprises an anti-cancer agent and/or antibody.

In an embodiment of the present disclosure, the pharmaceutical composition further comprises a pharmaceutically acceptable carrier, a diluent, and/or an excipient.

An embodiment of the present disclosure provides a therapeutic method for a disease, comprising administering an effective amount of a sequence, expression vector, host cell, virus, pharmaceutical composition, or medicament.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Hereinafter, the phrases "physiologically acceptable carrier" and "pharmaceutically acceptable carrier", which may be used interchangeably, refer to a carrier or a diluent that does not cause significant irritation to an organism and does not abrogate the biological activity and properties of the administered compound.

Techniques for formulation and administration of drugs may be found in the latest edition of "Remington's Pharmaceutical Sciences", Mack Publishing Co., Easton, Pa., which is herein fully incorporated by reference (Remington: The Science and Practice of Pharmacy, Gennaro, A., Lippincott, Williams & Wilkins, Philadelphia, Pa., 20th ed, 2000).

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

In an embodiment of the present disclosure, the pharmaceutical composition further comprises an antioxidant which can protect cells or macromolecules (e.g., the polysaccharide) from oxidative stress (oxidative damage caused by free radicals). Thus, the antioxidant can extend the survival of the macromolecules by preventing their oxidative depolymerization. Non-limiting examples of suitable antioxidants include molecules such as glutathione, vitamin C (sodium ascorbate), vitamin E (tocopherols and tocotrienols), N-Ac-L-cysteine, hydroquinone, glutamate, or enzymes such as catalase, superoxide dismutase, glutathione peroxidase or other peroxidases, and glucose-6-phosphate dehydrogenase (G6PD) (see Osmen I., Naziroglu M., Okutan R. Comparative study of antioxidant enzymes in tissues surrounding implant in rabbits. Cell. Biochem. Funct. 24:275-281, 2006).

Pharmaceutical compositions for potential administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

The compositions typically include one or more suitable diluents, fillers, salts, disintegrants, binders, lubricants, glidants, wetting agents, controlled release matrices, colorings, flavoring, carriers, excipients, buffers, stabilizers, solubilizers, commercial adjuvants, and/or other additives known in the art.

Alternatively, the active ingredient may be in powder form for constitution with a suitable vehicle, e.g., a sterile, pyrogen-free, water-based solution, before use.

The compositions, the pharmaceutical composition of the present disclosure may, if desired, be presented in a pack or dispenser device, such as an FDA approved kit, or an article of manufacture (with packaging material), which may contain one or more unit dosage forms containing the active ingredient. The pack may, for example, comprise metal or plastic foil, such as a blister pack. The pack or dispenser device may be accompanied by instructions for administration, implantation and/or treating a subject. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. The compositions, matrix or hydrogel of the invention formulated in a compatible pharmaceutical carrier may also be prepared, placed in an appropriate container, and labeled for treatment of an indicated condition, as is further detailed above.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

As used herein, the phrase "chemotherapeutic agent" refers to any chemical agent with therapeutic usefulness in the treatment of cancer. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these drugs are directly toxic to cancer cells and do not require immune stimulation. Suitable chemotherapeutic agents are described, for example, in Slapak and Kufe, Principles of Cancer Therapy, Chapter 86 in Harrison's Principles of Internal medicine, 14th edition; Perry et ah, Chemotherapeutic, Ch 17 in Abeloff, Clinical Oncology 2nd ed., 2000 ChrchillLivingstone, Inc.; Baltzer L. and Berkery R. (eds): Oncology Pocket Guide to Chemotherapeutic, 2nd ed. St. Luois, mosby-Year Book, 1995; Fischer D. S., Knobf M. F., Durivage H. J. (eds): The Cancer Chemotherapeutic Handbook, 4th ed. St. Luois, Mosby-Year Handbook.

The chemotherapeutic agent of the present invention can be, but not limited to, cytarabine (cytosine arabinoside, Ara-C, Cytosar-U), asprin, sulindac, curcumin, alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); thylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxy adenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics, such as actimomycin D, daunomycin (rubidomycin), doxorubicin, mitoxantrone, idarubicin, bleomycins, plicamycin (mithramycin), mitomycinC, and actinomycin; enzymes such as L-asparaginase, cytokines such as interferon (IFN)-gamma, tumor necrosis factor (TNF)-alpha, TNF-beta and GM-CSF, anti-angiogenic factors, such as angiostatin and endostatin, inhibitors of FGF or VEGF such as soluble forms of receptors for angiogenic factors, including soluble VGF/VEGF receptors, platinum coordination complexes such as cisplatin and carboplatin, anthracenediones such as mitoxantrone, substituted urea such as hydroxyurea, methylhydrazine derivatives including Nmethylhydrazine (MIH) and procarbazine, adrenocortical suppressants such as mitotane (o,ρ'-DDD) and aminoglutethimide; hormones and antagonists including adrenocortico steroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; non-steroidal antiandrogens such as flutamide; kinase inhibitors, histone deacetylase inhibitors, methylation inhibitors, proteasome inhibitors, monoclonal antibodies, oxidants, anti-oxidants, telomerase inhibitors, BH3 mimetics, ubiquitin ligase inhibitors, stat inhibitors and receptor tyrosin kinase inhibitors such as imatinib mesylate (marketed as Gleevac or Glivac) and erlotinib (an EGF receptor inhibitor) now marketed as Tarveca; and anti-virals such as oseltamivir phosphate, Amphotericin B, and palivizumab.

In some embodiments the daily dose the chemo therapeutic agent of the invention (e.g., cytarabine) or the pharmaceutical composition comprising same is ranging between 1 to 10 g per square meter of body area, between 1.5 to 5 g per square meter of body area or between 2 to 4 g per square meter of body area.

Various embodiments and aspects of the present invention as delineated hereinabove and as claimed in the claims section below find experimental support in the following examples.

Reference is now made to the following examples, which together with the above descriptions, illustrate the invention in a non-limiting fashion.

Example 1: A Virus that Obtains L025 Gene Deletion

Figure 6:
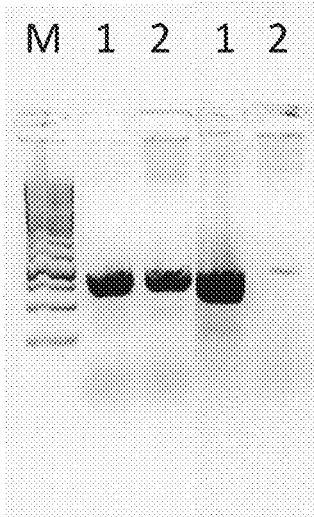
FIG. 6 shows recombinant virus with L025 gene deletion.

Please refer to FIG. 6, FIG. 6 shows recombinant virus with L025 gene deletion. M: is a molecular weight marker, 1: is a control virus, and 2 is a recombinant virus with L025 gene deletion. A46R is an amplified control gene fragment. L025 is a fragment of the L025 gene detected for deletion.

The virus with L025 gene deletion was obtained by homologous recombination using the VV Lister virus as the female parent and the shuttle vector for deleting the L025 gene. After the pure fluorescent infection spot was obtained by red fluorescence screening, small-scale virus amplification was carried out, and the viral DNA was extracted to identify the L025 gene deletion by PCR. A new virus with L025 gene deletion was obtained, as shown in FIG. 6.

Example 2: A Virus that Obtains L025 Gene Deletion and TK Gene Deletion

Figure 7:
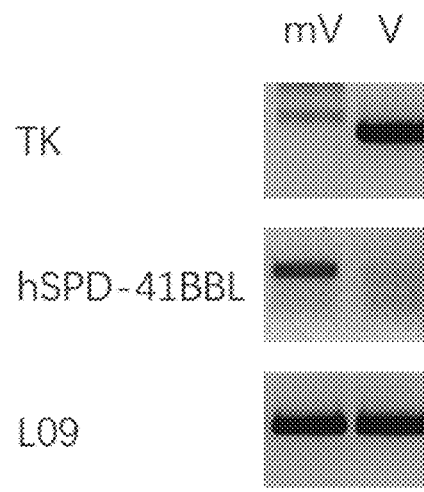
FIG. 7. Shows recombinant virus with TK gene deletion and hSPD-41BBL gene insertion.

The new virus with L025 gene deletion obtained in Example 1 contains the FRT site on both sides of the red fluorescent protein RFP. The Flipase was used to cleave the FRT site to delete the RFP gene, thus obtaining a new RFP-negative VV with deletion of the L025 gene. This virus was used as a backbone virus and a shuttle vector with TK gene deletion was used for homologous recombination to obtain a virus with TK gene deletion and simultaneously PD1 antibody gene insertion into this region. Small-scale virus amplification was performed after fluorescent screening to obtain pure virus-infected plaques, and viral DNA was extracted to identify TK gene deletion by PCR. A new virus with deletion in both L025 gene and the TK gene was obtained, and the PD1 antibody gene was inserted into the TK region (FIG. 7).

Example 3: A Virus with Deletion of L025 Gene, Deletion of TK Gene and Deletion of A46R Gene The new virus with L025 gene deletion and the TK gene deletion obtained in Example 2 contains Loxp sites on both sides of the red fluorescent protein RFP. The Loxp site was deleted by Cre recombinase to delete the RFP gene, thus obtaining the RFP-negative new virus with L025 and TK gene deletion. The virus was used as a backbone virus and a shuttle vector with A46R gene deletion was subjected to homologous recombination to obtain a virus with A46R gene deletion and simultaneous HIC1 gene insertion into this region. A small-scale virus amplification was carried out after green fluorescent screening to obtain pure virus-infected plaques, and viral DNA was extracted to identify A46R gene deletion by PCR. A new virus with L025 gene, TK gene and A46R gene deletion was obtained, and the PD1 antibody gene was inserted into the TK region, and the HIC1 gene was inserted into the A46R region, and the virus expressed green fluorescent protein GFP.

Example 4: A Virus Contains L025 Gene Deletion with IL21 and mB5R/sB5R Insertion in this Region; TK Gene Deletion with 4-1BBL Gene Insertion in this Region; A46R Gene Deletion with HIC1 Gene Insertion in this Region Please refer to FIGS. 14-15. FIG. 7 shows recombinant virus with TK gene deletion and hSPD-41BBL gene insertion. mV: is the modified virus, V: is the wild type virus, TK: is the amplified TK gene (negative results indicate that the gene has been deleted in the genome of the detected recombinant virus), hSPD-41BBL: is amplified inserted human SPD-41BBL positive result indicates that the gene has been inserted in the genome of the recombinant virus being tested), and L09: is an amplified control gene fragment.

Figure 8:
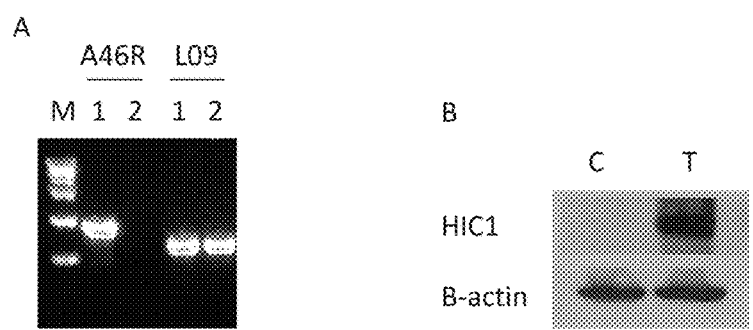
FIG. 8. Shows recombinant virus deletion of the A46R gene and viral expression of the inserted gene HIC1.

FIG. 8. Shows recombinant virus deletion of the A46R gene and viral expression of the inserted gene HIC1. A: PCR was used to identify the deletion of the A46R gene. M: is a molecular weight marker, 1: is a control virus, and 2 is a recombinant virus deleting the A46R gene. L09 is an amplified control gene fragment. B: Western blot analysis was used to identify the expression of HIC1 protein. C is a control virus, and T is a new recombinant virus carrying the HIC1 gene and deleting the A46R gene. HIC1 is the result of antibody detection, and 3-actin is a protein loading control.

The new virus with L025 gene, TK gene and the A46R gene deletion obtained in Example 3 was used as a backbone virus, and a shuttle vector for L025 gene deletion were homologously recombined to obtain the virus with L025 gene deletion and simultaneous IL21 and mB5R/sB5R gene insertion into this region. After the pure recombinant virus was obtained by fluorescence screening, small-scale virus was amplified, and the viral DNA was extracted and then the L025 gene deletion was identified by PCR. A new virus deleting the L025 gene, the TK gene and the A46R gene was obtained, and the 4-1BBL gene was inserted into the TK region, the HIC1 gene was inserted into the A46R region (FIG. 8), and the IL21 and mB5R/sB5R genes were inserted into the L025 region.

Example 5: A Panel of Solid Tumor Cells Infected by KM1 Virus

Figure 9A:
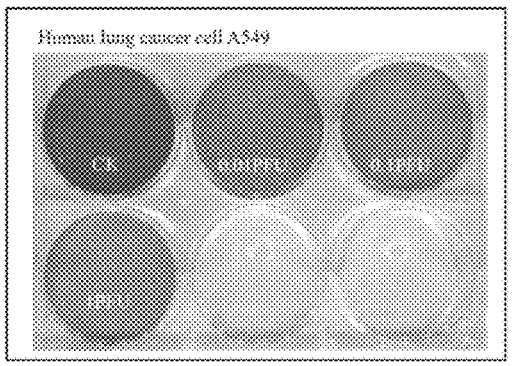
FIGS. 9A and 9B. KM1 killing of a panel of solid tumor cell lines with escalating dosage of the virus in 6-well plate for two days. The amount of virus used to infect the individual well were 0.01 pfu/cell, 0.1 pfu/cell, and 1 pfu/cell. Crystal violet was used to stain the remaining cells in the well when terminated the experiment.
Figure 9A:
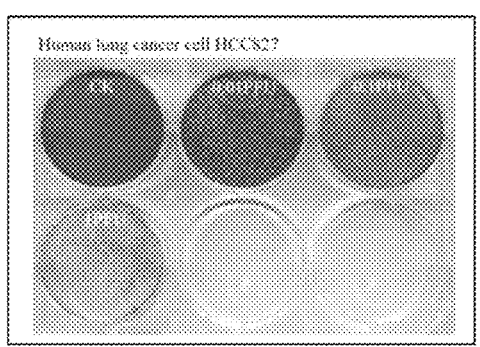
Figure 9A:
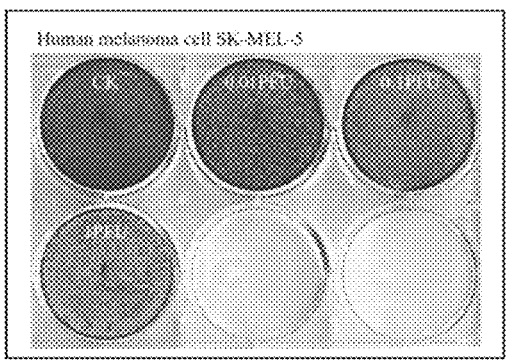
Figure 9A:
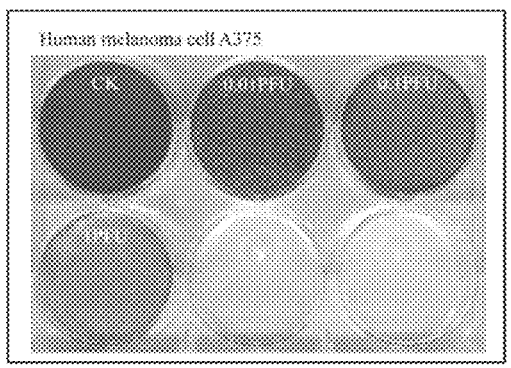
Figure 9A:
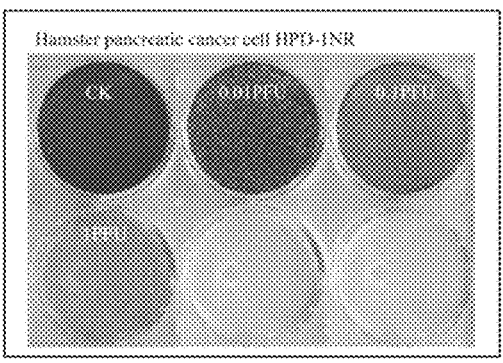
Figure 9A:
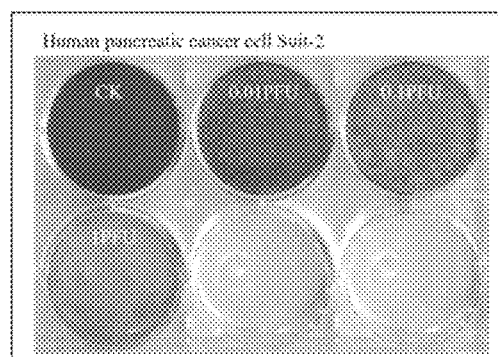
Figure 9A:
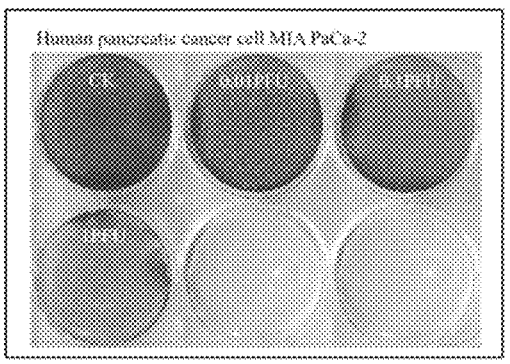
Figure 9A:
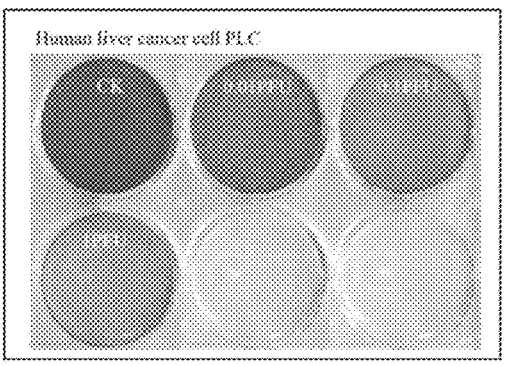
Figure 9B:
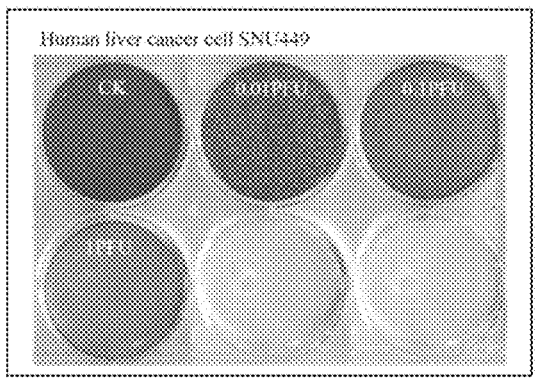
Figure 9B:
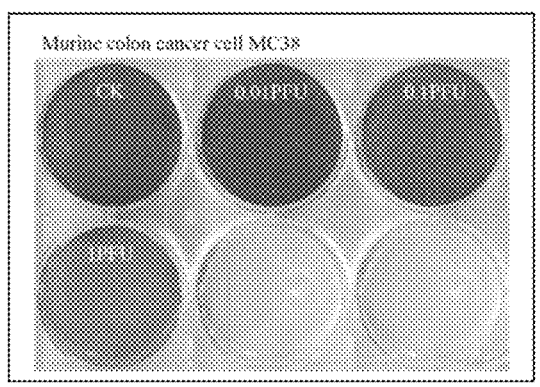
Figure 9B:
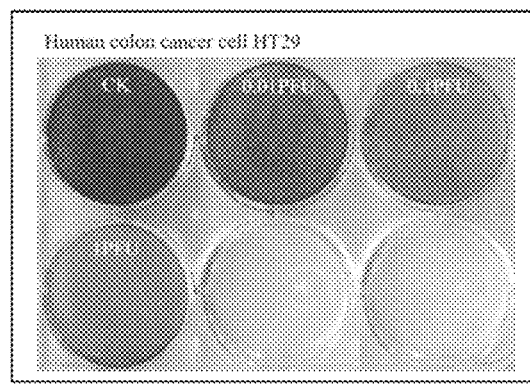
Figure 9B:
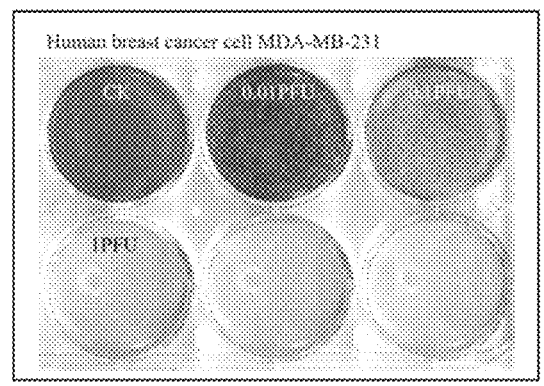
Figure 9B:
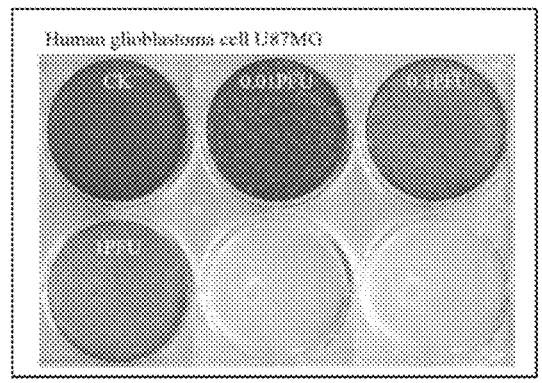
Figure 9B:
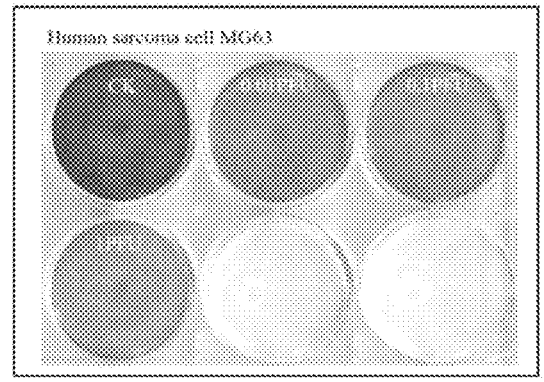
Figure 9B:
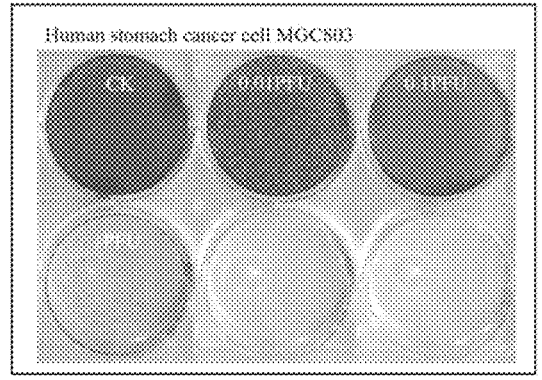
Figure 9B:
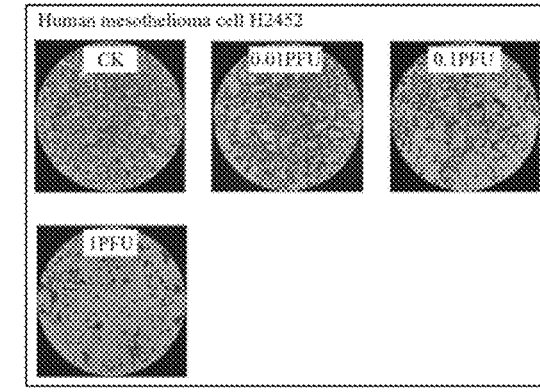

Please refer to FIGS. 9A-9B. FIGS. 9A-9B shows that KM1 killing of a panel of solid tumor cell lines with escalating dosage of the virus in 6-well plate for two days. The amount of virus used to infect the individual well were 0.01 pfu/cell, 0.1 pfu/cell, and 1 pfu/cell. Crystal violet was used to stain the remaining cells in the well when terminated the experiment.

Two days after virus infection at 0.01 pfu, 0.1 pfu and 1 pfu/cell, the cells were stained with crystal violet. The plates were scanned after staining, as shown in FIGS. 9A-9B.

Figure 10A:
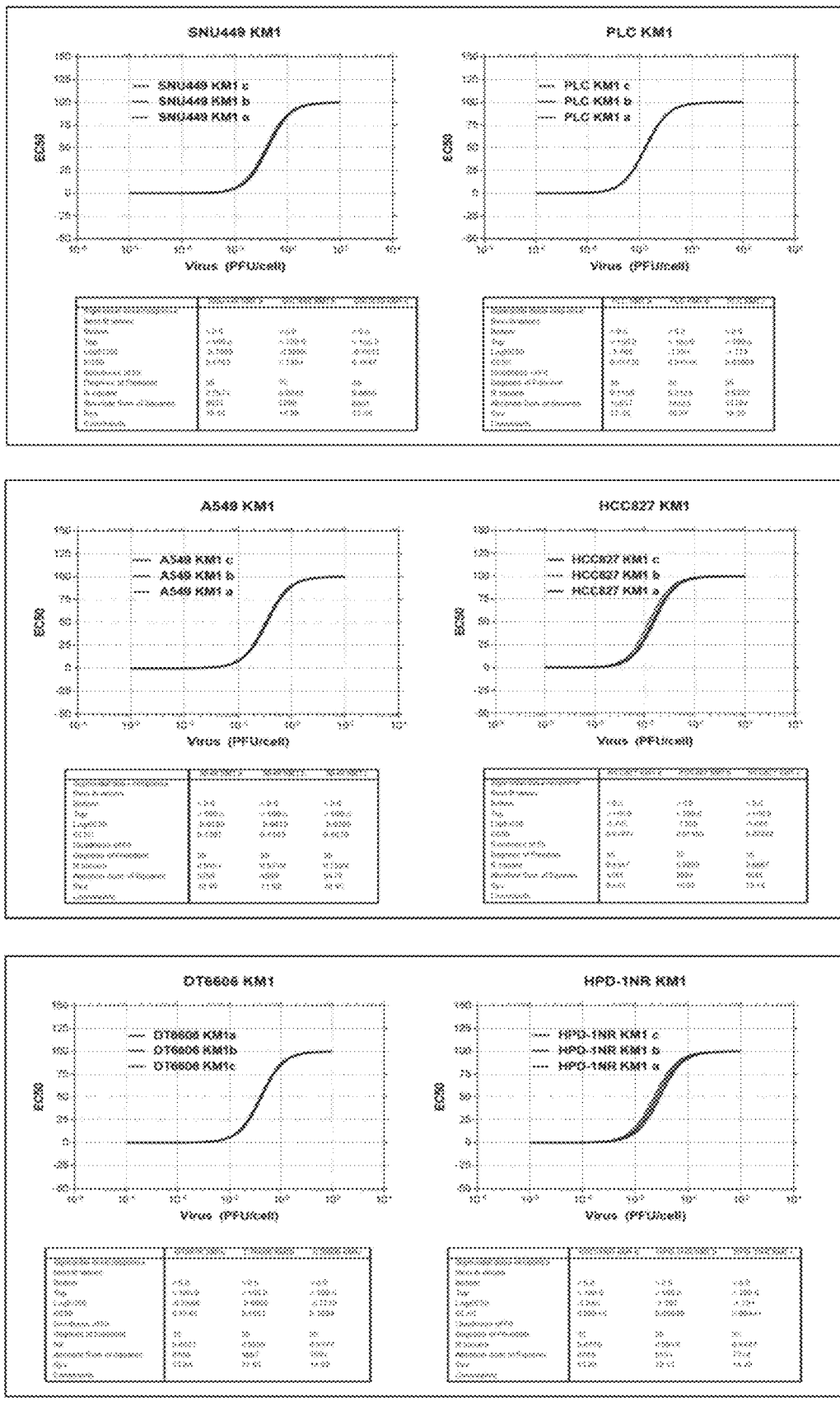
FIGS. 10A, 10B and 10C shows examples of EC50 assay on 17 cell lines.
Figure 10B:
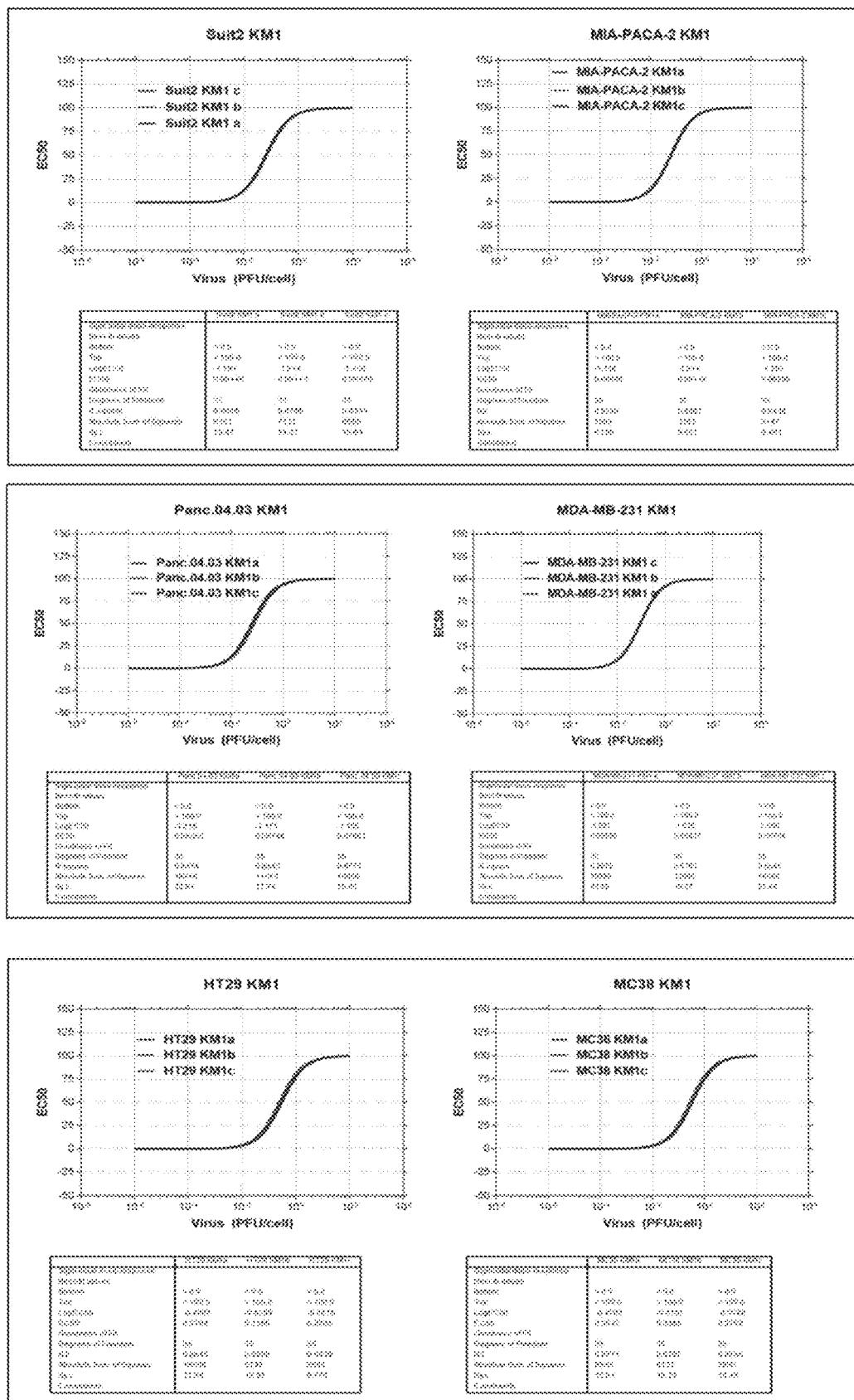
Figure 10C:
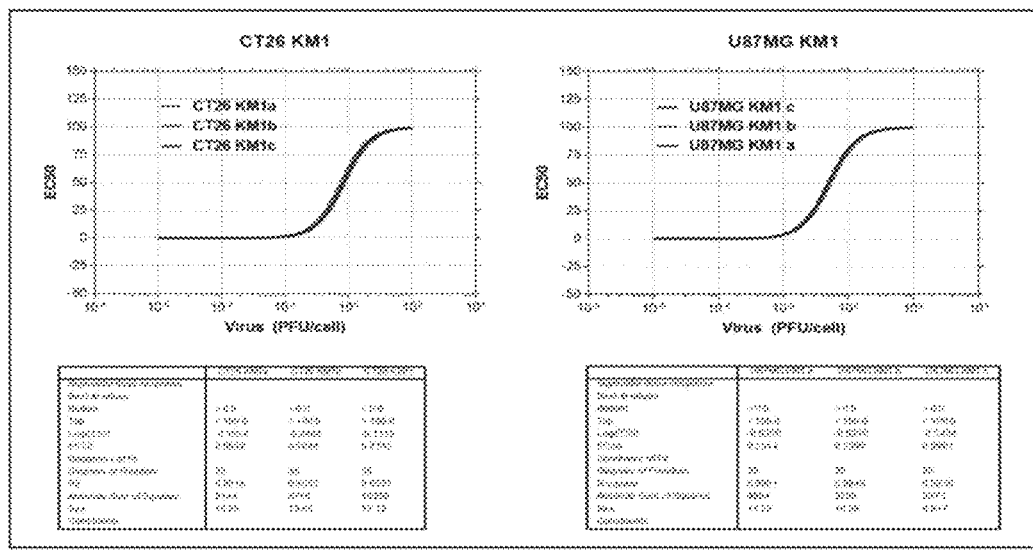
Figure 10C:
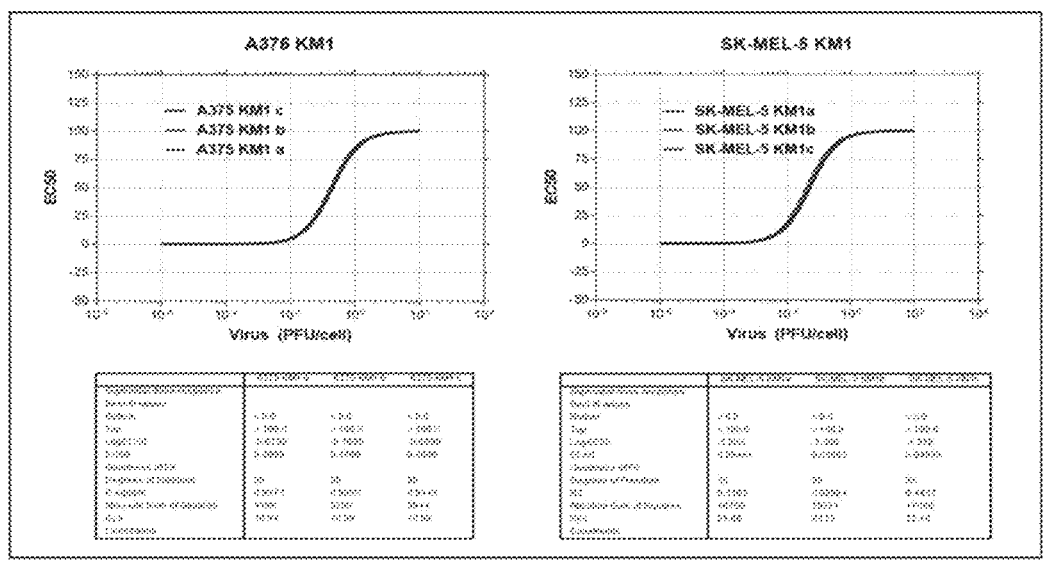
Figure 10C:
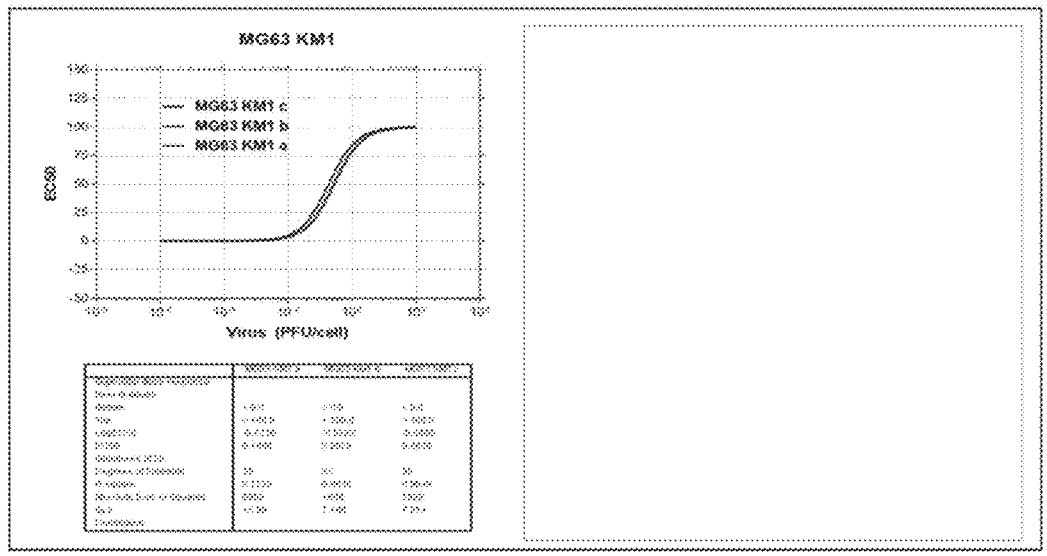
Figure 11:
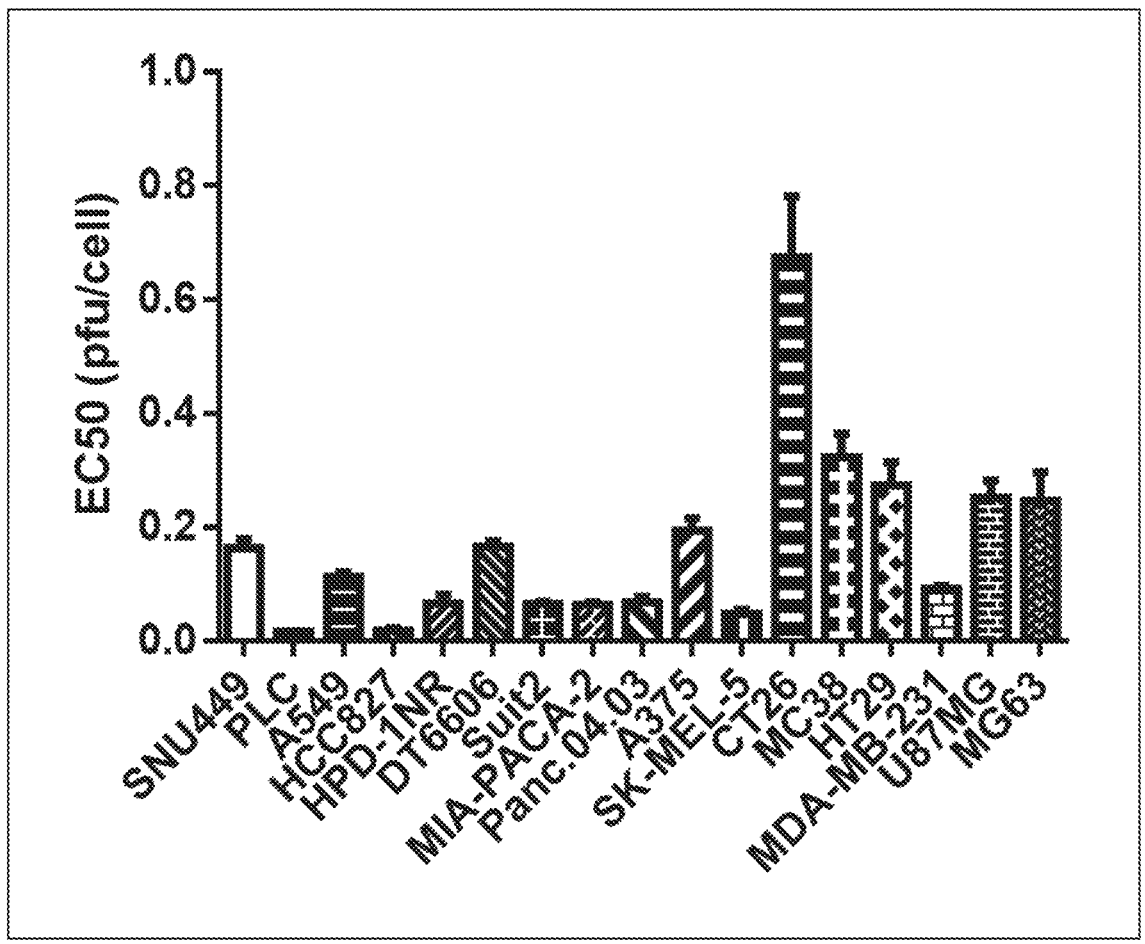
FIG. 11 shows the EC50 value for different cell lines.

Example 6: Solid Tumor Cells Sensitivity to KM1. A Panel of Solid Tumor Cells Infected by KM1 Virus in EC50 Assay Please refer to FIGS. 10A-11. FIGS. 10A-10C shows examples of EC50 assay on 17 cell lines, in which EC50 was performed in triplicate on the individual cell line. FIG. 11 shows the EC50 value for different cell lines.

Six days after virus infection cells viability was measured with MTS. The plates were read after incubation with MTS. (FIGS. 10A-10C and 11)

Example 7: Leukemia Cell Lines Sensitivity to KM1. A Panel of Leukemia Cell Lines were Infected by KM1

Please refer to FIG. 12. FIG. 12 shows killing of leukemia cell lines by vaccinia virus. EC50 assay performed on three cell lines (K562, C8166, THP-1) are provided as exemplary examples.

Subfigures A, B, and C show cell counting at the seeding point, 48 hours, and 72 hours post virus infection in control well (without virus infection, solid line) and virus infected well (donated line). Subfigure D shows the image of infected THP1 cells 48 hours post infection. Cells glowing with green fluorescence represents virus replicating/replicated in the cells.

The vaccinia virus of the present disclosure infected and killed majority of the leukemia cells in 72 hours. Live/dead cells were counted 24, 48 and 73 hours after virus infection. The results of selective sensitive cells were presented (FIG. 12).

Example 8: Leukemia Patient's Cells Sensitivity to KM1

Please refer to FIGS. 13-14. FIG. 13 shows examples of leukemia patients' white blood cells infected by KM1. FIG. 14 shows live/dead cells three days post KM1 infection.

Figure 13A:
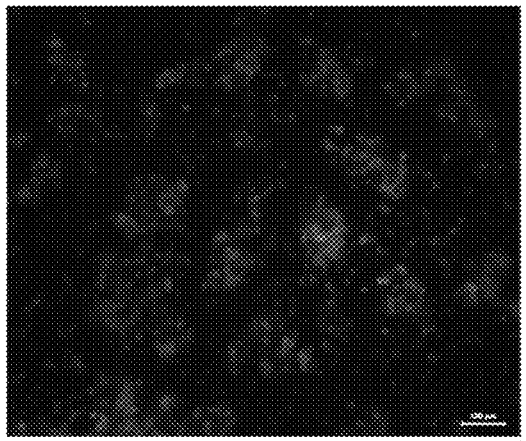
FIGS. 13A, 13B and 13C show examples of leukemia patients' white blood cells infected by KM1.
Figure 13A:
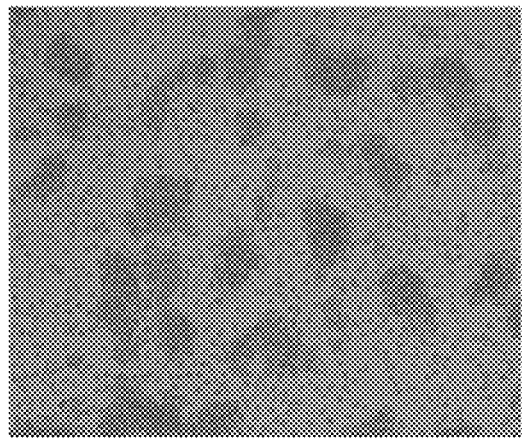
Figure 13B:
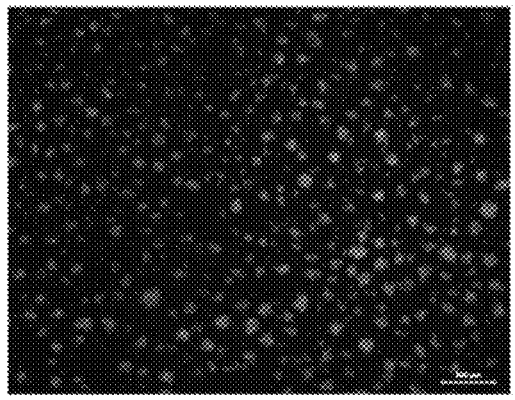
Figure 13B:
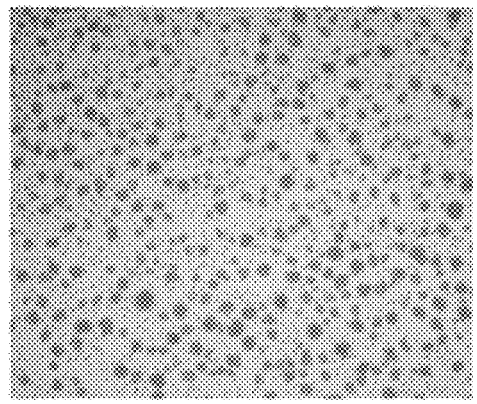
Figure 13C:
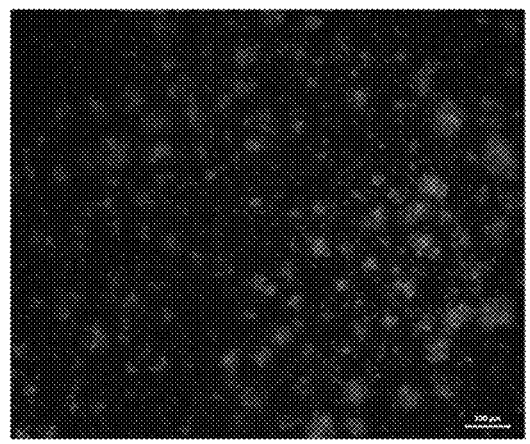
Figure 13C:
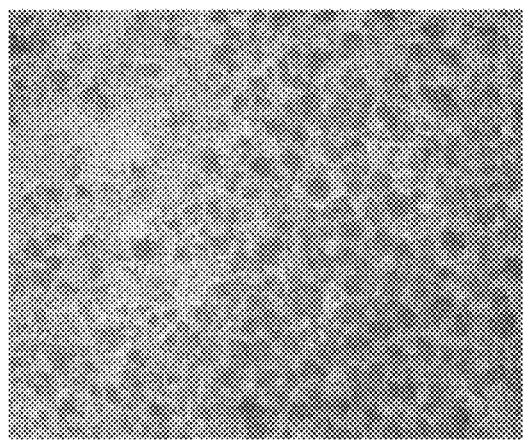

In FIG. 13A: sample from patient with CMML; FIG. 13B: sample from patient with M5b; and FIG. 13C: sample from patient with M4.

Figure 14A:
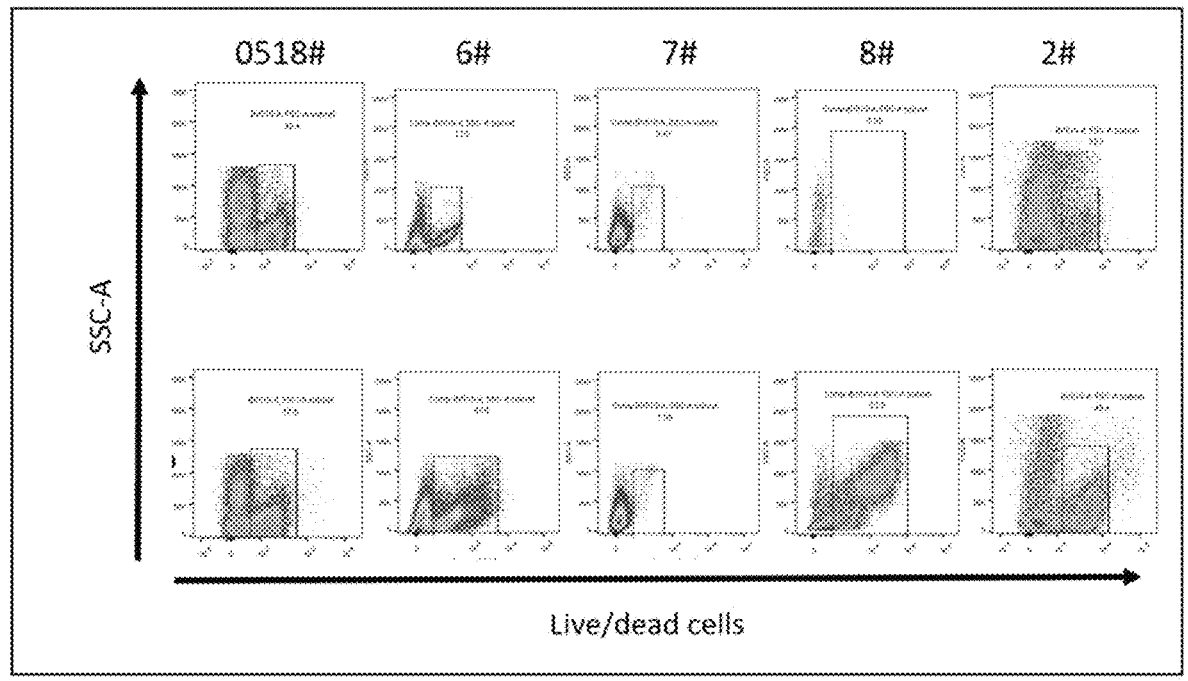
FIGS. 14A and 14B show live/dead cells three days post KM1 infection.
Figure 14B:
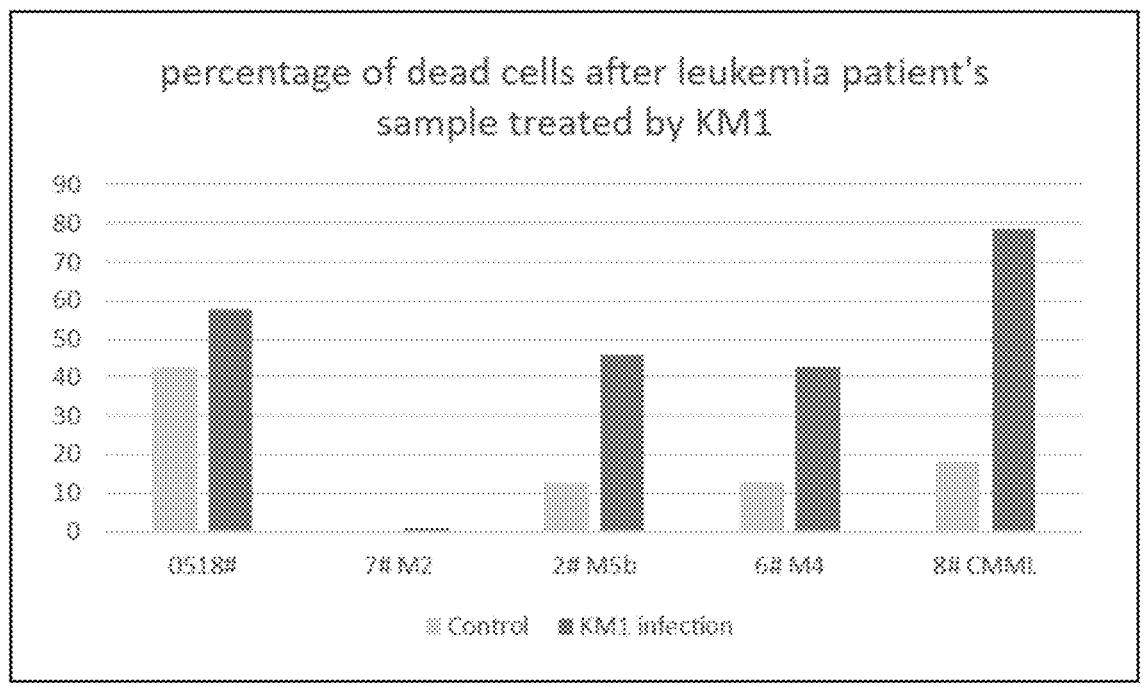

In FIG. 14A: FACs profiles of live/dead cells in control well (without KM1 infection, upper panel) and KM1 infected well of leukemia patients 0518#, 6#, 7#, 8# and 2#. FIG. 14B: dead cell percentages in control well (without KM1 infection, upper panel) and KM1 infected well of leukemia patients 0518#, 6#, 7#, 8# and 2#.

White blood cells from leukemia patients were infected. 72 hours post virus infection, cells were checked by fluorescence microscope and FACs. (FIGS. 13-14).

Example 9. KM1 Treatment of Syrian Golden Hamster Pancreatic Cancer

Figure 15:
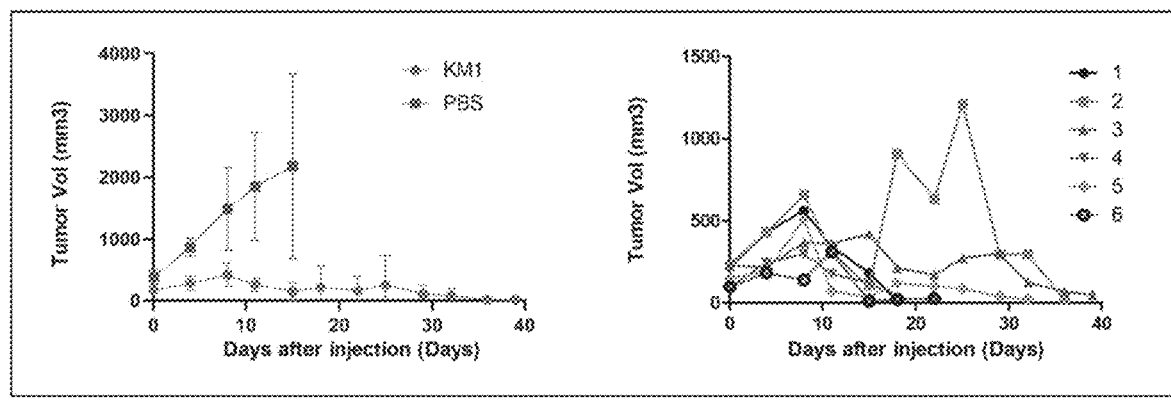
FIG. 15 shows anti-tumor efficacy of KM1 in Syrian hamster pancreatic cancer HPD 1NR model.

Please refer to FIG. 15, FIG. 15 shows anti-tumor efficacy of KM1 in Syrian hamster pancreatic cancer HPD 1NR model. The left panel shows tumor volume changes after treatment with KM1 and in control group without KM1 treatment. The right panel shows tumor volume changes in individual animal in the KM1 treatment group.

Example 10. HIC1 Armed Vaccinia Virus Treatment of Human Breast Cancer Cell MDA MB-231

Figure 16:
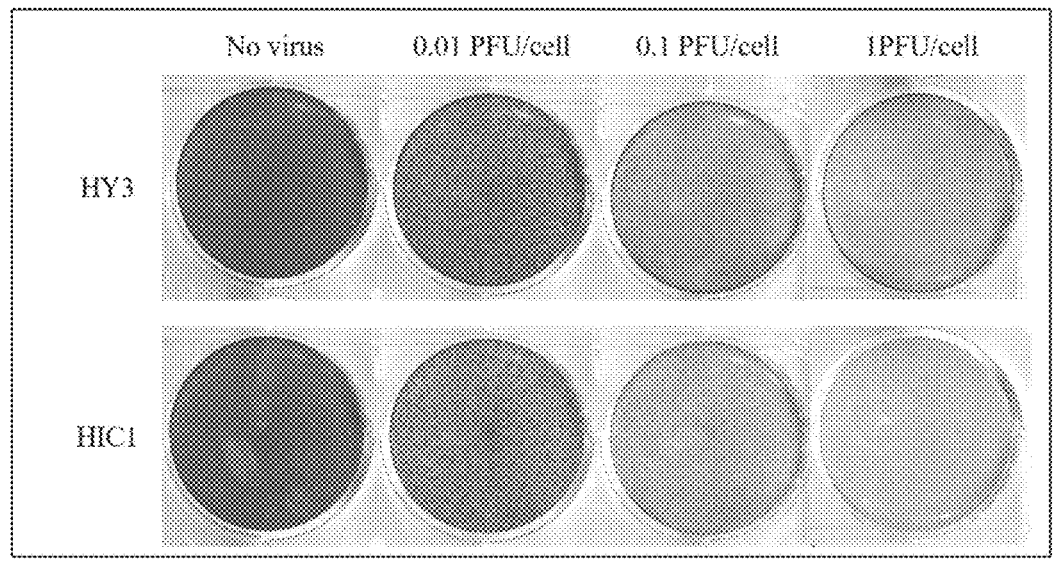
FIG. 16 shows treatment of human breast cancer cell MDA MB-231 using HIC1 armed vaccinia virus and its counterpart control HY3.
Figure 16:
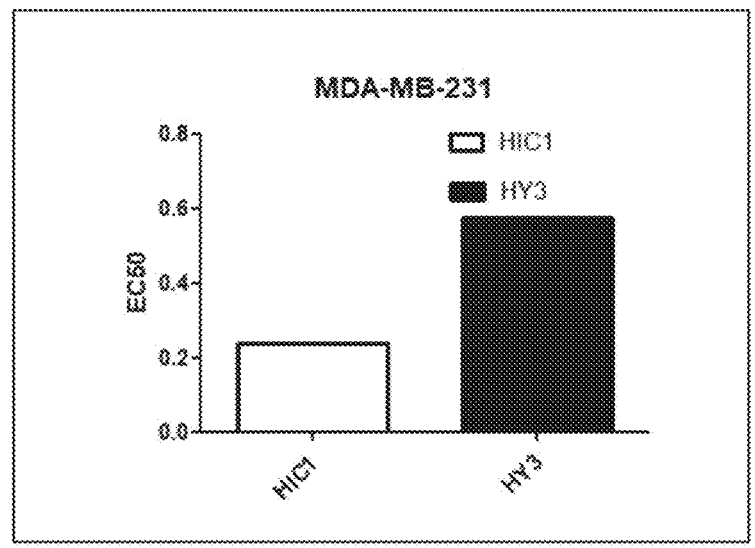

Please refer to FIG. 16, FIG. 16 shows treatment of human breast cancer cell MDA MB-231 using HIC1 armed vaccinia virus and its counterpart control HY3. Top panel shows treatment of human breast cancer cell MDA MB-231 using HIC1 armed vaccinia virus (HIC1) and its counterpart control HY3 on dose escalation in 6-well plate. Bottom panel shows EC50 calculated from the experiment of the top panel.

Accordingly, the present disclosure provides an engineered vaccinia virus, a pharmaceutical composition containing the same, and methods for use in treating a subject in need using the same. The engineered vaccinia virus includes deletion of a combination of viral genes and introduction of an immune co-stimulatory pathway activating molecule, immunomodulator gene, a truncated viral envelope gene, and/or a tumor suppressor into infected target cells. The oncolytic vaccinia virus of the present disclosure is capable of selectively infecting cancer cells, selectively replicating in tumor cells, selectively targeting tumor cells with activated EGFR/Ras/ERK pathway. The oncolytic vaccinia virus is also capable of inhibiting tumor-induced immunosuppression and activating of the NF Kappa B signaling pathway in immune cells. The oncolytic vaccinia virus is also capable of invoking anti-tumor immune response, enhancing the proliferation and cytotoxicity of T cells. The oncolytic vaccinia virus is also capable of inhibiting tumor progression. The oncolytic vaccinia virus may integrate a tumor suppressor gene into genome of cancer cells that underexpress or loss the tumor suppressor gene.

As used herein the term "about" refers to ±10%.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "treating" refers to arresting the development of a pathology (disease, disorder or condition) and/or causing the reduction, remission, or regression of a pathology. Those of skill in the art will understand that various methodologies and assays can be used to assess the reduction, remission or regression of a pathology. It will be appreciated that the treating may be performed alone or in conjunction with other therapies.

As used herein, the term "preventing" refers to keeping a disease, disorder or condition from occurring in a subject who may be at risk for the disease, but does not yet display symptoms of the disease disorder or condition or has not yet been diagnosed as having the disease, disorder or condition. Those of skill in the art will understand that various methodologies and assays can be used to assess the development of a pathology.

As used herein, the terms "subject" or "subject in need thereof" include mammals, preferably human beings at any age or gender. The subject may be showing preliminary signs of a pathology, e.g. a disease, disorder or condition associated with a mutant or a nonfunctional HIC1 protein, e.g., hyperproliferative disease.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO:3 is expressed in a DNA sequence format (e.g., reciting T for thymine), but it can refer to either a DNA sequence that corresponds to a WNT3A nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

In summary, people with ordinary skills in the art may make various changes and modifications according to the technical solutions and technical concept of the present application, and all such changes and modifications fall into the protection scope of claims appended to the present application.

What is claimed is:

1. An engineered vaccinia virus, comprising
a mutated viral sequence for selective replication in tumor cells and/or activation of immune cells; and
heterologous sequences for encoding a cytokine and an immune co-stimulatory pathway activating molecule,
wherein the heterologous sequences are stably incorporated into the genome of the engineered vaccinia virus,
wherein the mutated viral sequence comprises mutations of deletions in L025, TK, and A46R,
wherein the cytokine is IL-21,
wherein the immune co-stimulatory pathway activating molecule is 4-1BB ligand.

2. The engineered vaccinia virus according to claim 1, wherein the heterologous sequence is stably incorporated into the mutated viral sequence of the engineered vaccinia virus.

3. The engineered vaccinia virus according to claim 1, wherein the heterologous sequence further encodes a truncated viral envelope gene, and/or a tumor suppressor, wherein the truncated viral envelope gene is B5R containing a short consensus repeats (SCR) 2, SCR3, and SCR4 domains deletion.

4. The engineered vaccinia virus according to claim 1, wherein the heterologous sequence comprises at least one of:
(a) a sequence set forth in SEQ ID NO: 2;
(b) a sequence set forth in SEQ ID NO: 4;
(c) a sequence set forth in SEQ ID NO: 6;
(d) a sequence set forth in SEQ ID NO: 8;
(e) a sequence set forth in SEQ ID NO: 10;
(f) a sequence set forth in SEQ ID NO: 12; or
(g) a sequence set forth in SEQ ID NO: 14.

5. The engineered vaccinia virus according to claim 1, wherein the heterologous sequence encodes at least one of:
(a) a sequence set forth in SEQ ID NO: 1;
(b) a sequence set forth in SEQ ID NO: 3;
(c) a sequence set forth in SEQ ID NO: 5;
(d) a sequence set forth in SEQ ID NO: 7;
(e) a sequence set forth in SEQ ID NO: 9;
(f) a sequence set forth in SEQ ID NO: 11; or
(g) a sequence set forth in SEQ ID NO: 13.

6. The engineered vaccinia virus according to claim 1, wherein the engineered vaccinia virus comprises a sequence of formula: 5'-$A_1$-X-$A_2$-$B_1$-Y-$B_2$-$C_1$-Z-$C_2$-3', wherein $A_1$ and $A_2$ are a left arm and a right arm of a first viral gene respectively, $B_1$ and $B_2$ are a left arm and a right arm of a second viral gene, respectively, $C_1$ and $C_2$ are a left arm and a right arm of a third viral gene, respectively, wherein X, Y, and Z are heterologous genes, each selected from one of cytokines, immune co-stimulatory pathway activating, truncated viral envelope genes, and tumor suppressor genes.

7. The engineered vaccinia virus according to claim 6, wherein the first viral gene is L025, the second viral gene is TK, and the third viral gene is A46R.

8. The engineered vaccinia virus according to claim 3, wherein the mutated viral sequence comprises mutations of deletions in L025, TK, and A46R, and the heterologous sequence comprises a hybrid gene of IL-21 and modified B5R, and 4-1BBL.

9. The engineered vaccinia virus according to claim 1, wherein the engineered vaccinia virus is selected from the group consisting of Lister, Western Reserve (WR), Copenhagen (Cop), Bern, Paris, Tashkent, Tian Tan, Wyeth (DRY-VAX), IHD-J, IHD-W, Brighton, Ankara, CVA382, modified vaccinia ankara (MVA), Dairen I, LC16m8, LC16M0, LIVP, ACAM2000, WR 65-16, Connaught, New York City Board of Health (NYCBH), EM-63 and NYVAC strain.

10. A pharmaceutical composition comprising an effective amount of the engineered vaccinia virus of claim 1 and a pharmaceutical acceptable carrier.

11. The pharmaceutical composition according to claim 10, wherein the pharmaceutical composition is formulated for oral, topical, parenteral delivery, or interventional therapy.

12. The pharmaceutical composition according to claim 10, wherein the pharmaceutical composition is formulated for topical intratumoral injection, topical intra-artery injection, intraperitoneal injection, intrathoracic injection, systemic intravenous injection, intramuscular injection, subcutaneous injection, intrathecal injections, direct intraventricular injection, intracardiac injection, or intranasal injections.

13. The pharmaceutical composition according to claim 10, wherein the engineered vaccinia virus can be used alone as monotherapy; or wherein the engineered vaccinia virus can be used in combination with anti-cancer agent, immune suppressors, and/or oncolytic virus enhancers.

14. The pharmaceutical composition according to claim 10, wherein the engineered vaccinia virus can be used in combination with 5-fluorouracil (FU), folinic acid (FA), methotrexate, capecitabine, oxaliplatin, bevacizumab, cetuximab, immune checkpoint inhibitors, other types of oncolytic viruses, or any combination thereof.

15. An engineered vaccinia virus for use in inducing cancer cells death, regulating a biological activity of the cancer cells, regulating immune response, enhancing proliferation of T cells, and/or cytotoxicity of T cells, wherein the engineered vaccinia virus is as provided in claim 1.

16. An engineered vaccinia virus for use in inducing cancer cells death, regulating a biological activity of the cancer cells, regulating immune response, enhancing proliferation of T cells, and/or cytotoxicity of T cells wherein the biological activity of the cancer cells comprises inhibition of cancer cells replication, inhibition of cancer cells division, inhibition of DNA repair of cancer cells, inhibition of cancer cells migration, or promoting cancer death, wherein the engineered vaccinia virus is as provided in claim 1.

17. An engineered vaccinia virus for use in the manufacture of a medicament for treating lung cancer, melanoma, pancreatic cancer, liver cancer, colon cancer, breast cancer, glioblastoma, sarcoma, stomach cancer, ovarian cancer, mesothelioma, and leukemia, wherein the engineered vaccinia virus is as provided in claim 1.

18. An engineered vaccinia virus for use in the manufacture of a medicament for suppressing cancer cells growth, inducing cancer cells death, and/or regulating a biological activity of the cancer cells, wherein the engineered vaccinia virus is as provided in claim 1.

* * * * *

```
                        SEQUENCE LISTING

<160> NUMBER OF SEQ ID NOS: 28

<210> SEQ ID NO 1
<211> LENGTH: 100
<212> TYPE: PRT
<213> ORGANISM: Vaccinia virus
<220> FEATURE:
<221> NAME/KEY: Artificial sequence
<222> LOCATION: (1)..(100)
<223> OTHER INFORMATION: mB5R amino acid sequence

<400> SEQUENCE: 1

Met Lys Thr Ile Ser Val Val Thr Leu Leu Cys Val Leu Pro Ala Val
1               5                   10                  15

Val Tyr Ser Cys Val Arg Thr Asn Glu Lys Phe Asp Pro Val Asp Asp
            20                  25                  30

Gly Pro Asp Asp Glu Thr Asp Leu Ser Lys Leu Ser Lys Asp Val Val
        35                  40                  45

Gln Tyr Glu Gln Glu Ile Glu Ser Leu Glu Ala Thr Tyr His Ile Ile
    50                  55                  60

Ile Val Ala Leu Thr Ile Met Gly Val Ile Phe Leu Ile Ser Val Ile
65                  70                  75                  80

Val Leu Val Cys Ser Cys Asp Lys Asn Asn Asp Gln Tyr Lys Phe His
                85                  90                  95

Lys Leu Leu Pro
            100

<210> SEQ ID NO 2
<211> LENGTH: 303
<212> TYPE: DNA
<213> ORGANISM: Vaccinia virus
<220> FEATURE:
<221> NAME/KEY: Artificial sequence
<222> LOCATION: (1)..(303)
<223> OTHER INFORMATION: mB5R nucleotide sequence

<400> SEQUENCE: 2
atgaaaacga tttccgttgt tacgttgtta tgcgtactac ctgctgttgt ttattcatgt      60
gtacgaacta acgaaaaatt tgatccagtg gatgatggtc ccgacgatga gacagatttg     120
agcaaactct cgaaagacgt tgtacaatat gaacaagaaa tagaatcgtt agaagcaact     180
tatcatataa tcatagtggc gttgacaatt atgggcgtca tattttttaat ctccgttata     240 gtattagttt gttcctgtga caaaaataat gaccaatata agttccataa attgctaccg     300
tga                                                                   303

<210> SEQ ID NO 3
<211> LENGTH: 153
<212> TYPE: PRT
<213> ORGANISM: Vaccinia virus
<220> FEATURE:
<221> NAME/KEY: Artificial sequence
<222> LOCATION: (1)..(153)
<223> OTHER INFORMATION: sB5R amino acid sequence

<400> SEQUENCE: 3
```

-continued

```
Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Gln Gly Tyr His Ser Ser Asp Pro Asn Ala Val Cys Glu Thr Asp
    50                  55                  60

Lys Trp Lys Tyr Glu Asn Pro Cys Cys Val Arg Thr Asn Glu Lys Phe
65                  70                  75                  80

Asp Pro Val Asp Asp Gly Pro Asp Asp Glu Thr Asp Leu Ser Lys Leu
                85                  90                  95

Ser Lys Asp Val Val Gln Tyr Glu Gln Glu Ile Glu Ser Leu Glu Ala
            100                 105                 110

Thr Tyr His Ile Ile Ile Val Ala Leu Thr Ile Met Gly Val Ile Phe
        115                 120                 125

Leu Ile Ser Val Ile Val Leu Val Cys Ser Cys Asp Lys Asn Asn Asp
    130                 135                 140

Gln Tyr Lys Phe His Lys Leu Leu Pro
145                 150

<210> SEQ ID NO 4
<211> LENGTH: 462
<212> TYPE: DNA
<213> ORGANISM: Vaccinia virus
<220> FEATURE:
<221> NAME/KEY: Artificial sequence
<222> LOCATION: (1)..(462)
<223> OTHER INFORMATION: sB5R nucleotide sequence

<400> SEQUENCE: 4
atgaaaacga tttccgttgt tacgttgtta tgcgtactac ctgctgttgt ttattcaaca      60
tgtactgtac ccactatgaa taacgctaaa ttaacgtcta ccgaaacatc gtttaatgat     120
aaacagaaag ttacatttac atgtgatcag ggatatcatt cttcggatcc aaatgctgtc     180
tgcgaaacag ataaatggaa atacgaaaat ccatgctgtg tacgaactaa cgaaaaattt     240
gatccagtgg atgatggtcc cgacgatgag acagatttga gcaaactctc gaaagacgtt     300
gtacaatatg aacaagaaat agaatcgtta gaagcaactt atcatataat catagtggcg     360
ttgacaatta tgggcgtcat atttttaatc tccgttatag tattagtttg ttcctgtgac     420
aaaaataatg accaatataa gttccataaa ttgctaccgt ga                        462

<210> SEQ ID NO 5
<211> LENGTH: 462
<212> TYPE: PRT
<213> ORGANISM: Mus musculus
<220> FEATURE:
<221> NAME/KEY: Artificial sequence
<222> LOCATION: (1)..(462)
<223> OTHER INFORMATION: SPD-m4-1BBL amino acid sequence

<400> SEQUENCE: 5

Met Leu Pro Phe Leu Ser Met Leu Val Leu Leu Val Gln Pro Leu Gly
1               5                   10                  15

Asn Leu Gly Ala Glu Met Lys Ser Leu Ser Gln Arg Ser Val Pro Asn
            20                  25                  30

Thr Cys Thr Leu Val Met Cys Ser Pro Thr Glu Asn Gly Leu Pro Gly
        35                  40                  45
```

```
Arg Asp Gly Arg Asp Gly Arg Glu Gly Pro Arg Gly Glu Lys Gly Asp
 50                  55                  60
Pro Gly Leu Pro Gly Pro Met Gly Leu Ser Gly Leu Gln Gly Pro Thr
 65                  70                  75                  80
Gly Pro Val Gly Pro Lys Gly Glu Asn Gly Ser Ala Gly Glu Pro Gly
                     85                  90                  95
Pro Lys Gly Glu Arg Gly Leu Ser Gly Pro Gly Leu Pro Gly Ile
                 100                 105                 110
Pro Gly Pro Ala Gly Lys Glu Gly Pro Ser Gly Lys Gln Gly Asn Ile
                 115                 120                 125
Gly Pro Gln Gly Lys Pro Gly Pro Lys Gly Glu Ala Gly Pro Lys Gly
                 130                 135                 140
Glu Val Gly Ala Pro Gly Met Gln Gly Ser Thr Gly Ala Lys Gly Ser
145                 150                 155                 160
Thr Gly Pro Lys Gly Glu Arg Gly Ala Pro Gly Val Gln Gly Ala Pro
                 165                 170                 175
Gly Asn Ala Gly Ala Ala Gly Pro Ala Gly Pro Ala Gly Pro Gln Gly
                 180                 185                 190
Ala Pro Gly Ser Arg Gly Pro Pro Gly Leu Lys Gly Asp Arg Gly Val
                 195                 200                 205
Pro Gly Asp Arg Gly Ile Lys Gly Glu Ser Gly Leu Pro Asp Ser Ala
                 210                 215                 220
Ala Leu Arg Gln Gln Met Glu Ala Leu Lys Gly Lys Leu Gln Arg Leu
225                 230                 235                 240
Glu Val Ala Phe Ser His Tyr Gln Lys Ala Ala Leu Phe Pro Asp Gly
                 245                 250                 255
Arg Thr Glu Pro Arg Pro Ala Leu Thr Ile Thr Thr Ser Pro Asn Leu
                 260                 265                 270
Gly Thr Arg Glu Asn Asn Ala Asp Gln Val Thr Pro Val Ser His Ile
                 275                 280                 285
Gly Cys Pro Asn Thr Thr Gln Gln Gly Ser Pro Val Phe Ala Lys Leu
                 290                 295                 300
Leu Ala Lys Asn Gln Ala Ser Leu Cys Asn Thr Thr Leu Asn Trp His
305                 310                 315                 320
Ser Gln Asp Gly Ala Gly Ser Ser Tyr Leu Ser Gln Gly Leu Arg Tyr
                 325                 330                 335
Glu Glu Asp Lys Lys Glu Leu Val Val Asp Ser Pro Gly Leu Tyr Tyr
                 340                 345                 350
Val Phe Leu Glu Leu Lys Leu Ser Pro Thr Phe Thr Asn Thr Gly His
                 355                 360                 365
Lys Val Gln Gly Trp Val Ser Leu Val Leu Gln Ala Lys Pro Gln Val
                 370                 375                 380
Asp Asp Phe Asp Asn Leu Ala Leu Thr Val Glu Leu Phe Pro Cys Ser
385                 390                 395                 400
Met Glu Asn Lys Leu Val Asp Arg Ser Trp Ser Gln Leu Leu Leu Leu
                 405                 410                 415
Lys Ala Gly His Arg Leu Ser Val Gly Leu Arg Ala Tyr Leu His Gly
                 420                 425                 430
Ala Gln Asp Ala Tyr Arg Asp Trp Glu Leu Ser Tyr Pro Asn Thr Thr
                 435                 440                 445
Ser Phe Gly Leu Phe Leu Val Lys Pro Asp Asn Pro Trp Glu
450                 455                 460
```

<210> SEQ ID NO 6
<211> LENGTH: 1389
<212> TYPE: DNA
<213> ORGANISM: Mus musculus
<220> FEATURE:
<221> NAME/KEY: Artificial sequence
<222> LOCATION: (1)..(1389)
<223> OTHER INFORMATION: SPD-m4-1BBL nucleotide sequence

<400> SEQUENCE: 6

```
atgctgccct ttctctccat gcttgtcttg cttgtacagc ccctgggaaa tctgggagca      60
gaaatgaaga gcctctcgca gagatcagta cccaacacct gcaccctagt catgtgtagc     120
ccaacagaga atggcctgcc tggtcgtgat ggacgggatg ggagagaagg tccacggggt     180
gagaagggtg atccaggttt gccaggacct atggggctct cagggttgca gggccctaca     240
ggtccagttg gacccaaagg agagaatggc tctgctggcg aacctggacc aaagggagaa     300
cgtggactaa gtggacctcc aggacttcca ggtattcctg gtccagctgg aaagaaggt      360
ccctctggga gcaggggaa cataggacct caaggcaaac caggtcctaa aggagaggct      420
gggcccaaag gagaagtagg tgctcctggc atgcaaggat ctacaggggc aaaaggctcc     480
acaggcccca agggagaaag aggtgcccct ggtgtgcaag agccccagg aatgctgga      540
gcagcaggac ctgccggacc tgccggtcca cagggagctc caggttccag ggggccccca     600
ggactcaagg gggacagagg tgttcctgga cacagaggaa tcaaaggtga agcgggctt      660
ccagacagtg ctgctctgag cagcagatg gaggccttaa aggaaaaact acagcgtcta      720
gaggttgcct ctcccacta tcagaaagct gcattgttcc ctgatggccg caccgagcct     780
cggccagcgc tcacaatcac cacctcgccc aacctgggta cccgagagaa taatgcagac     840
caggtcaccc ctgttttccca cattggctgc cccaacacta cacaacaggg ctctcctgtg    900
ttcgccaagc tactggctaa aaaccaagca tcgttgtgca atacaactct gaactggcac     960
agccaagatg gagctgggag ctcatacctc tctcaaggtc tgaggtacga agaagacaaa    1020
aaggagttgg tggtagacag tcccgggctc tactacgtat ttttggaact gaagctcagt   1080
ccaacattca caaacacagg ccacaaggtg cagggctggg tctctcttgt ttgcaagca    1140
aagcctcagg tagatgactt tgacaacttg gccctgacag tggaactgtt cccttgctcc   1200
atggagaaca agttagtgga ccgttcctgg agtcaactgt tgctcctgaa ggctggccac   1260
cgcctcagtg tgggtctgag gcttatctg catggagccc aggatgcata cagagactgg   1320
gagctgtctt atcccaacac caccagcttt ggactcttc ttgtgaaacc cgacaaccca   1380
tgggaatga                                                          1389
```

<210> SEQ ID NO 7
<211> LENGTH: 463
<212> TYPE: PRT
<213> ORGANISM: Homo sapiens
<220> FEATURE:
<221> NAME/KEY: Artificial sequence
<222> LOCATION: (1)..(463)
<223> OTHER INFORMATION: SPD-h4-1BBL amino acid sequence

<400> SEQUENCE: 7

```
Met Leu Leu Phe Leu Leu Ser Ala Leu Val Leu Thr Gln Pro Leu
1               5                   10                  15

Gly Tyr Leu Glu Ala Glu Met Lys Thr Tyr Ser His Arg Thr Met Pro
            20                  25                  30

Ser Ala Cys Thr Leu Val Met Cys Ser Ser Val Glu Ser Gly Leu Pro
        35                  40                  45
```

```
Gly Arg Asp Gly Arg Asp Gly Arg Glu Gly Pro Arg Gly Glu Lys Gly
            50                  55                  60

Asp Pro Gly Leu Pro Gly Ala Ala Gly Gln Ala Gly Met Pro Gly Gln
 65                  70                  75                  80

Ala Gly Pro Val Gly Pro Lys Gly Asp Asn Gly Ser Val Gly Glu Pro
                     85                  90                  95

Gly Pro Lys Gly Asp Thr Gly Pro Ser Gly Pro Gly Pro Pro Gly Gly
            100                 105                 110

Val Pro Gly Pro Ala Gly Arg Glu Gly Pro Leu Gly Lys Gln Gly Asn
            115                 120                 125

Ile Gly Pro Gln Gly Lys Pro Gly Pro Lys Gly Glu Ala Gly Pro Lys
            130                 135                 140

Gly Glu Val Gly Ala Pro Gly Met Gln Gly Ser Ala Gly Ala Arg Gly
145                 150                 155                 160

Leu Ala Gly Pro Lys Gly Glu Arg Gly Val Pro Gly Glu Arg Gly Val
                    165                 170                 175

Pro Gly Asn Thr Gly Ala Ala Gly Ser Ala Gly Ala Met Gly Pro Gln
            180                 185                 190

Gly Ser Pro Gly Ala Arg Gly Pro Pro Gly Leu Lys Gly Asp Lys Gly
            195                 200                 205

Ile Pro Gly Asp Lys Gly Ala Lys Gly Glu Ser Gly Leu Pro Asp Val
            210                 215                 220

Ala Ser Leu Arg Gln Gln Val Glu Ala Leu Gln Gly Gln Val Gln His
225                 230                 235                 240

Leu Gln Ala Ala Phe Ser Gln Tyr Lys Lys Val Glu Leu Phe Pro Asn
                    245                 250                 255

Gly Leu Ala Cys Pro Trp Ala Val Ser Gly Ala Arg Ala Ser Pro Gly
            260                 265                 270

Ser Ala Ala Ser Pro Arg Leu Arg Glu Gly Pro Glu Leu Ser Pro Asp
            275                 280                 285

Asp Pro Ala Gly Leu Leu Asp Leu Arg Gln Gly Met Phe Ala Gln Leu
            290                 295                 300

Val Ala Gln Asn Val Leu Leu Ile Asp Gly Pro Leu Ser Trp Tyr Ser
305                 310                 315                 320

Asp Pro Gly Leu Ala Gly Val Ser Leu Thr Gly Gly Leu Ser Tyr Lys
                    325                 330                 335

Glu Asp Thr Lys Glu Leu Val Val Ala Lys Ala Gly Val Tyr Tyr Val
            340                 345                 350

Phe Phe Gln Leu Glu Leu Arg Arg Val Val Ala Gly Glu Gly Ser Gly
            355                 360                 365

Ser Val Ser Leu Ala Leu His Leu Gln Pro Leu Arg Ser Ala Ala Gly
            370                 375                 380

Ala Ala Ala Leu Ala Leu Thr Val Asp Leu Pro Pro Ala Ser Ser Glu
385                 390                 395                 400

Ala Arg Asn Ser Ala Phe Gly Phe Gln Gly Arg Leu Leu His Leu Ser
                    405                 410                 415

Ala Gly Gln Arg Leu Gly Val His Leu His Thr Glu Ala Arg Ala Arg
            420                 425                 430

His Ala Trp Gln Leu Thr Gln Gly Ala Thr Val Leu Gly Leu Phe Arg
            435                 440                 445

Val Thr Pro Glu Ile Pro Ala Gly Leu Pro Ser Pro Arg Ser Glu
450                 455                 460
```

<210> SEQ ID NO 8
<211> LENGTH: 1392
<212> TYPE: DNA
<213> ORGANISM: Homo sapiens
<220> FEATURE:
<221> NAME/KEY: Artificial sequence
<222> LOCATION: (1)..(1392)
<223> OTHER INFORMATION: SPD-h4-1BBL nucleotide sequence

<400> SEQUENCE: 8

```
atgctgctct tcctcctctc tgcactggtc ctgctcacac agcccctggg ctacctggaa      60
gcagaaatga agacctactc ccacagaaca atgcccagtg cttgcaccct ggtcatgtgt     120
agctcagtgg agagtggcct gcctggtcgc gatggacggg atgggagaga gggccctcgg    180
ggcgagaagg gggacccagg tttgccagga gctgcagggc aagcagggat gcctggacaa    240
gctggcccag ttgggcccaa aggggacaat ggctctgttg gagaacctgg accaaaggga    300
gacactgggc caagtggacc tccaggacct cccgtgtgc ctggtccagc tggaagagaa     360
ggtccctgg ggaagcaggg aacatagga cctcagggca agccaggccc aaaaggagaa      420
gctgggccca aggagaagt aggtgcccca ggcatgcagg gctcggcagg ggcaagaggc      480
ctcgcaggcc ctaagggaga gcgaggtgtc cctggtgagc gtggagtccc tggaaacaca    540
ggggcagcag ggtctgctgg agccatgggt ccccagggaa gtccaggtgc aggggacccc    600
ccgggattga aggggacaa aggcattcct ggagacaaag agcaaaggg agaaagtggg       660
cttccagatg ttgcttctct gaggcagcag gttgaggcct acagggaca gtacagcac      720
ctccaggctg ctttctctca gtataagaaa gttgagctct cccaaatgg cctcgcctgc    780
ccctgggccg tgtccggggc tcgcgcctcg cccggctccg cggccagccc gagactccgc   840
gagggtcccg agctttcgcc cgacgatccc gccggcctct ggacctgcg caggggcatg    900
tttgcgcagc tggtggccca aaatgttctg ctgatcgatg gcccctgag ctggtacagt    960
gacccaggcc tggcaggcgt gtccctgacg gggggcctga gctacaaaga ggacacgaag   1020
gagctggtgg tggccaaggc tggagtctac tatgtcttct ttcaactaga gctgcggcgc   1080
gtggtggccg gcgagggctc aggctccgtt tcacttgcgc tgcacctgca gccactcgc    1140
tctgctgctg ggccgccgc cctggctttg accgtggacc tgccacccgc ctcctccgag   1200
gctcggaact cggccttcgg tttccagggc gcttgctgc acctgagtgc cggccagcgc    1260
ctgggcgtcc atcttcacac tgaggccagg gcacgccatg cctggcagct acccagggc    1320
gccacagtct tgggactctt ccgggtgacc cccgaaatcc cagccggact cccttcaccg   1380
aggtcggaat aa                                                        1392
```

<210> SEQ ID NO 9
<211> LENGTH: 146
<212> TYPE: PRT
<213> ORGANISM: Mus musculus
<220> FEATURE:
<221> NAME/KEY: PEPTIDE
<222> LOCATION: (1)..(146)
<223> OTHER INFORMATION: mIL-21 amino acid sequence

<400> SEQUENCE: 9

Met Glu Arg Thr Leu Val Cys Leu Val Val Ile Phe Leu Gly Thr Val
1               5                   10                  15

Ala His Lys Ser Ser Pro Gln Gly Pro Asp Arg Leu Leu Ile Arg Leu
            20                  25                  30

Arg His Leu Ile Asp Ile Val Glu Gln Leu Lys Ile Tyr Glu Asn Asp

```
                35                  40                  45
Leu Asp Pro Glu Leu Leu Ser Ala Pro Gln Asp Val Lys Gly His Cys
 50                  55                  60

Glu His Ala Ala Phe Ala Cys Phe Gln Lys Ala Lys Leu Lys Pro Ser
 65                  70                  75                  80

Asn Pro Gly Asn Asn Lys Thr Phe Ile Ile Asp Leu Val Ala Gln Leu
                 85                  90                  95

Arg Arg Arg Leu Pro Ala Arg Arg Gly Gly Lys Lys Gln Lys His Ile
            100                 105                 110

Ala Lys Cys Pro Ser Cys Asp Ser Tyr Glu Lys Arg Thr Pro Lys Glu
        115                 120                 125

Phe Leu Glu Arg Leu Lys Trp Leu Leu Gln Lys Met Ile His Gln His
    130                 135                 140

Leu Ser
145

<210> SEQ ID NO 10
<211> LENGTH: 441
<212> TYPE: DNA
<213> ORGANISM: Mus musculus
<220> FEATURE:
<221> NAME/KEY: exon
<222> LOCATION: (1)..(441)
<223> OTHER INFORMATION: mIL-21 nucleotide sequence

<400> SEQUENCE: 10 atg gag agg acc ctt gtc tgt ctg gta gtc atc ttc ttg ggg aca gtg      48
Met Glu Arg Thr Leu Val Cys Leu Val Val Ile Phe Leu Gly Thr Val
 1               5                  10                  15 gcc cat aaa tca agc ccc caa ggg cca gat cgc ctc ctg att aga ctt      96
Ala His Lys Ser Ser Pro Gln Gly Pro Asp Arg Leu Leu Ile Arg Leu
                 20                  25                  30 cgt cac ctt att gac att gtt gaa cag ctg aaa atc tat gaa aat gac     144
Arg His Leu Ile Asp Ile Val Glu Gln Leu Lys Ile Tyr Glu Asn Asp
             35                  40                  45 ttg gat cct gaa ctt cta tca gct cca caa gat gta aag ggg cac tgt     192
Leu Asp Pro Glu Leu Leu Ser Ala Pro Gln Asp Val Lys Gly His Cys
 50                  55                  60 gag cat gca gct ttt gcc tgt ttt cag aag gcc aaa ctc aag cca tca     240
Glu His Ala Ala Phe Ala Cys Phe Gln Lys Ala Lys Leu Lys Pro Ser
 65                  70                  75                  80 aac cct gga aac aat aag aca ttc atc att gac ctc gtg gcc cag ctc     288
Asn Pro Gly Asn Asn Lys Thr Phe Ile Ile Asp Leu Val Ala Gln Leu
                 85                  90                  95 agg agg agg ctg cct gcc agg agg gga gga aag aaa cag aag cac ata     336
Arg Arg Arg Leu Pro Ala Arg Arg Gly Gly Lys Lys Gln Lys His Ile
            100                 105                 110 gct aaa tgc cct tcc tgt gat tcg tat gag aaa agg aca ccc aaa gaa     384
Ala Lys Cys Pro Ser Cys Asp Ser Tyr Glu Lys Arg Thr Pro Lys Glu
        115                 120                 125 ttc cta gaa aga cta aaa tgg ctc ctt caa aag atg att cat cag cat     432
Phe Leu Glu Arg Leu Lys Trp Leu Leu Gln Lys Met Ile His Gln His
    130                 135                 140 ctc tcc tga                                                          441
Leu Ser
145

<210> SEQ ID NO 11
<211> LENGTH: 162
<212> TYPE: PRT
```

```
<213> ORGANISM: Homo sapiens
<220> FEATURE:
<221> NAME/KEY: PEPTIDE
<222> LOCATION: (1)..(162)
<223> OTHER INFORMATION: hIL--21 amino acid sequence

<400> SEQUENCE: 11

Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
                35                  40                  45

Leu Lys Asn Tyr Val Asn Asp Leu Val Pro Glu Phe Leu Pro Ala Pro
            50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
            115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 12
<211> LENGTH: 489
<212> TYPE: DNA
<213> ORGANISM: Homo sapiens
<220> FEATURE:
<221> NAME/KEY: exon
<222> LOCATION: (1)..(489)
<223> OTHER INFORMATION: hIL-21 nucleotide sequence

<400> SEQUENCE: 12 atg aga tcc agt cct ggc aac atg gag agg att gtc atc tgt ctg atg    48
Met Arg Ser Ser Pro Gly Asn Met Glu Arg Ile Val Ile Cys Leu Met
1               5                   10                  15 gtc atc ttc ttg ggg aca ctg gtc cac aaa tca agc tcc caa ggt caa    96
Val Ile Phe Leu Gly Thr Leu Val His Lys Ser Ser Gln Gly Gln
            20                  25                  30 gat cgc cac atg att aga atg cgt caa ctt ata gat att gtt gat cag   144
Asp Arg His Met Ile Arg Met Arg Gln Leu Ile Asp Ile Val Asp Gln
                35                  40                  45 ctg aaa aat tat gtg aat gac ttg gtc cct gaa ttt ctg cca gct cca   192
Leu Lys Asn Tyr Val Asn Asp Leu Val Pro Glu Phe Leu Pro Ala Pro
            50                  55                  60 gaa gat gta gag aca aac tgt gag tgg tca gct ttt tcc tgc ttt cag   240
Glu Asp Val Glu Thr Asn Cys Glu Trp Ser Ala Phe Ser Cys Phe Gln
65                  70                  75                  80 aag gcc caa cta aag tca gca aat aca gga aac aat gaa agg ata atc   288
Lys Ala Gln Leu Lys Ser Ala Asn Thr Gly Asn Asn Glu Arg Ile Ile
                85                  90                  95 aat gta tca att aaa aag ctg aag agg aaa cca cct tcc aca aat gca   336
Asn Val Ser Ile Lys Lys Leu Lys Arg Lys Pro Pro Ser Thr Asn Ala
            100                 105                 110
```

```
ggg aga aga cag aaa cac aga cta aca tgc cct tca tgt gat tct tat    384
Gly Arg Arg Gln Lys His Arg Leu Thr Cys Pro Ser Cys Asp Ser Tyr
            115                 120                 125 gag aaa aaa cca ccc aaa gaa ttc cta gaa aga ttc aaa tca ctt ctc    432
Glu Lys Lys Pro Pro Lys Glu Phe Leu Glu Arg Phe Lys Ser Leu Leu
    130                 135                 140 caa aag atg att cat cag cat ctg tcc tct aga aca cac gga agt gaa    480
Gln Lys Met Ile His Gln His Leu Ser Ser Arg Thr His Gly Ser Glu
145                 150                 155                 160 gat tcc tag                                                        489
Asp Ser

<210> SEQ ID NO 13
<211> LENGTH: 714
<212> TYPE: PRT
<213> ORGANISM: Homo sapiens
<220> FEATURE:
<221> NAME/KEY: PEPTIDE
<222> LOCATION: (1)..(714)

<400> SEQUENCE: 13
```

Met Leu Asp Thr Met Glu Ala Pro Gly His Ser Arg Gln Leu Leu
1               5                   10                  15

Gln Leu Asn Asn Gln Arg Thr Lys Gly Phe Leu Cys Asp Val Ile Ile
            20                  25                  30

Val Val Gln Asn Ala Leu Phe Arg Ala His Lys Asn Val Leu Ala Ala
        35                  40                  45

Ser Ser Ala Tyr Leu Lys Ser Leu Val Val His Asp Asn Leu Leu Asn
    50                  55                  60

Leu Asp His Asp Met Val Ser Pro Ala Val Phe Arg Leu Val Leu Asp
65                  70                  75                  80

Phe Ile Tyr Thr Gly Arg Leu Ala Asp Gly Ala Glu Ala Ala Ala Ala
                85                  90                  95

Ala Ala Val Ala Pro Gly Ala Glu Pro Ser Leu Gly Ala Val Leu Ala
            100                 105                 110

Ala Ala Ser Tyr Leu Gln Ile Pro Asp Leu Val Ala Leu Cys Lys Lys
        115                 120                 125

Arg Leu Lys Arg His Gly Lys Tyr Cys His Leu Arg Gly Gly Gly Gly
    130                 135                 140

Gly Gly Gly Gly Tyr Ala Pro Tyr Gly Arg Pro Gly Arg Gly Leu Arg
145                 150                 155                 160

Ala Ala Thr Pro Val Ile Gln Ala Cys Tyr Pro Ser Pro Val Gly Pro
                165                 170                 175

Pro Pro Pro Pro Ala Ala Glu Pro Pro Ser Gly Pro Glu Ala Ala Val
            180                 185                 190

Asn Thr His Cys Ala Glu Leu Tyr Ala Ser Gly Pro Gly Pro Ala Ala
        195                 200                 205

Ala Leu Cys Ala Ser Glu Arg Arg Cys Ser Pro Leu Cys Gly Leu Asp
    210                 215                 220

Leu Ser Lys Lys Ser Pro Gly Ser Ala Ala Pro Glu Arg Pro Leu
225                 230                 235                 240

Ala Glu Arg Glu Leu Pro Arg Pro Asp Ser Pro Ser Ala Gly
                245                 250                 255

Pro Ala Ala Tyr Lys Glu Pro Pro Leu Ala Leu Pro Ser Leu Pro Pro
            260                 265                 270

Leu Pro Phe Gln Lys Leu Glu Glu Ala Ala Pro Pro Ser Asp Pro Phe

-continued

```
                275                 280                 285
Arg Gly Gly Ser Gly Ser Pro Gly Pro Glu Pro Pro Gly Arg Pro Asp
        290                 295                 300
Gly Pro Ser Leu Leu Tyr Arg Trp Met Lys His Glu Pro Gly Leu Gly
305                 310                 315                 320
Ser Tyr Gly Asp Glu Leu Gly Arg Glu Arg Gly Ser Pro Ser Glu Arg
                325                 330                 335
Cys Glu Glu Arg Gly Gly Asp Ala Ala Val Ser Pro Gly Gly Pro Pro
            340                 345                 350
Leu Gly Leu Ala Pro Pro Arg Tyr Pro Gly Ser Leu Asp Gly Pro
            355                 360                 365
Gly Ala Gly Gly Asp Gly Asp Asp Tyr Lys Ser Ser Glu Glu Thr
370                 375                 380
Gly Ser Ser Glu Asp Pro Ser Pro Gly Gly His Leu Glu Gly Tyr
385                 390                 395                 400
Pro Cys Pro His Leu Ala Tyr Gly Glu Pro Glu Ser Phe Gly Asp Asn
            405                 410                 415
Leu Tyr Val Cys Ile Pro Cys Gly Lys Gly Phe Pro Ser Ser Glu Gln
            420                 425                 430
Leu Asn Ala His Val Glu Ala His Val Glu Glu Glu Ala Leu Tyr
            435                 440                 445
Gly Arg Ala Glu Ala Ala Glu Val Ala Ala Gly Ala Ala Gly Leu Gly
450                 455                 460
Pro Pro Phe Gly Gly Gly Gly Asp Lys Val Ala Gly Ala Pro Gly Gly
465                 470                 475                 480
Leu Gly Glu Leu Leu Arg Pro Tyr Arg Cys Ala Ser Cys Asp Lys Ser
                485                 490                 495
Tyr Lys Asp Pro Ala Thr Leu Arg Gln His Glu Lys Thr His Trp Leu
            500                 505                 510
Thr Arg Pro Tyr Pro Cys Thr Ile Cys Gly Lys Lys Phe Thr Gln Arg
            515                 520                 525
Gly Thr Met Thr Arg His Met Arg Ser His Leu Gly Leu Lys Pro Phe
        530                 535                 540
Ala Cys Asp Ala Cys Gly Met Arg Phe Thr Arg Gln Tyr Arg Leu Thr
545                 550                 555                 560
Glu His Met Arg Ile His Ser Gly Glu Lys Pro Tyr Glu Cys Gln Val
                565                 570                 575
Cys Gly Gly Lys Phe Ala Gln Gln Arg Asn Leu Ile Ser His Met Lys
            580                 585                 590
Met His Ala Val Gly Gly Ala Ala Gly Ala Ala Gly Ala Leu Ala Gly
            595                 600                 605
Leu Gly Gly Leu Pro Gly Val Pro Gly Pro Asp Gly Lys Gly Lys Leu
            610                 615                 620
Asp Phe Pro Glu Gly Val Phe Ala Val Ala Arg Leu Thr Ala Glu Gln
625                 630                 635                 640
Leu Ser Leu Lys Gln Gln Asp Lys Ala Ala Ala Glu Leu Leu Ala
                645                 650                 655
Gln Thr Thr His Phe Leu His Asp Pro Lys Val Ala Leu Glu Ser Leu
            660                 665                 670
Tyr Pro Leu Ala Lys Phe Thr Ala Glu Leu Gly Leu Ser Pro Asp Lys
            675                 680                 685
Ala Ala Glu Val Leu Ser Gln Gly Ala His Leu Ala Ala Gly Pro Asp
            690                 695                 700
```

```
Gly Arg Thr Ile Asp Arg Phe Ser Pro Thr
705                 710
```

<210> SEQ ID NO 14
<211> LENGTH: 2145
<212> TYPE: DNA
<213> ORGANISM: Homo sapiens
<220> FEATURE:
<221> NAME/KEY: exon
<222> LOCATION: (1)..(2145)
<223> OTHER INFORMATION: HIC1 nucleotide sequence

<400> SEQUENCE: 14

```
atg ctg gac acg atg gag gcg ccc ggc cac tcc agg cag ctg ctg ctg        48
Met Leu Asp Thr Met Glu Ala Pro Gly His Ser Arg Gln Leu Leu Leu
1               5                   10                  15 cag ctc aac aac cag cgc acc aag ggc ttc ttg tgc gac gtg atc atc        96
Gln Leu Asn Asn Gln Arg Thr Lys Gly Phe Leu Cys Asp Val Ile Ile
                20                  25                  30 gtg gtg cag aac gcc ctc ttc cgc gcg cac aag aac gtg ctg gcg gcc       144
Val Val Gln Asn Ala Leu Phe Arg Ala His Lys Asn Val Leu Ala Ala
            35                  40                  45 agc agc gcc tac ctc aag tcc ctg gtg gtg cat gac aac ctg ctc aac       192
Ser Ser Ala Tyr Leu Lys Ser Leu Val Val His Asp Asn Leu Leu Asn
        50                  55                  60 ctg gac cat gac atg gtg agc ccg gcc gtg ttc cgc ctg gtg ctg gac       240
Leu Asp His Asp Met Val Ser Pro Ala Val Phe Arg Leu Val Leu Asp
65                  70                  75                  80 ttc atc tac acc ggc cgc ctg gct gac ggc gca gag gcg gct gcg gcc       288
Phe Ile Tyr Thr Gly Arg Leu Ala Asp Gly Ala Glu Ala Ala Ala Ala
                85                  90                  95 gcg gcc gtg gcc ccg ggg gct gag ccg agc ctg ggc gcc gtg ctg gcc       336
Ala Ala Val Ala Pro Gly Ala Glu Pro Ser Leu Gly Ala Val Leu Ala
                100                 105                 110 gcc gcc agc tac ctg cag atc ccc gac ctc gtg gcg ctg tgc aag aaa       384
Ala Ala Ser Tyr Leu Gln Ile Pro Asp Leu Val Ala Leu Cys Lys Lys
            115                 120                 125 cgc ctc aag cgc cac ggc aag tac tgc cac ctg cgg ggc ggc ggc ggc       432
Arg Leu Lys Arg His Gly Lys Tyr Cys His Leu Arg Gly Gly Gly Gly
        130                 135                 140 ggc ggc ggc ggc tac gcg ccc tat ggt cgg ccg ggc cgg ggc ctg cgg       480
Gly Gly Gly Gly Tyr Ala Pro Tyr Gly Arg Pro Gly Arg Gly Leu Arg
145                 150                 155                 160 gcc gcc acg ccg gtc atc cag gcc tgc tac ccg tcc cca gtc ggg cct       528
Ala Ala Thr Pro Val Ile Gln Ala Cys Tyr Pro Ser Pro Val Gly Pro
                165                 170                 175 ccg ccg ccg cct gcc gcg gag ccg ccc tcg ggc cca gag gcc gcg gtc       576
Pro Pro Pro Pro Ala Ala Glu Pro Pro Ser Gly Pro Glu Ala Ala Val
                180                 185                 190 aac acg cac tgc gcc gag ctg tac gcg tcg gga ccc ggc ccg gcc gcc       624
Asn Thr His Cys Ala Glu Leu Tyr Ala Ser Gly Pro Gly Pro Ala Ala
            195                 200                 205 gca ctc tgt gcc tcg gag cgc cgc tgc tcc cct ctt tgt ggc ctg gac       672
Ala Leu Cys Ala Ser Glu Arg Arg Cys Ser Pro Leu Cys Gly Leu Asp
        210                 215                 220 ctg tcc aag aag agc ccg ccg ggc tcc gcg gcg cca gag cgg ccg ctg       720
Leu Ser Lys Lys Ser Pro Pro Gly Ser Ala Ala Pro Glu Arg Pro Leu
225                 230                 235                 240 gct gag cgc gag ctg ccc ccg cgc ccg gac agc cct ccc agc gcc ggc       768
Ala Glu Arg Glu Leu Pro Pro Arg Pro Asp Ser Pro Pro Ser Ala Gly
                245                 250                 255
```

```
                                              -continued ccc gcc gcc tac aag gag ccg cct ctc gcc ctg ccg tcg ctg ccg ccg      816
Pro Ala Ala Tyr Lys Glu Pro Pro Leu Ala Leu Pro Ser Leu Pro Pro
        260                 265                 270 ctg ccc ttc cag aag ctg gag gag gcc gca ccg cct tcc gac cca ttt      864
Leu Pro Phe Gln Lys Leu Glu Glu Ala Ala Pro Pro Ser Asp Pro Phe
        275                 280                 285 cgc ggc ggc agc ggc agc ccg gga ccc gag ccc ccc ggc cgc ccc gac      912
Arg Gly Gly Ser Gly Ser Pro Gly Pro Glu Pro Pro Gly Arg Pro Asp
        290                 295                 300 ggg cct agt ctc ctc tat cgc tgg atg aag cac gag ccg ggc ctg ggt      960
Gly Pro Ser Leu Leu Tyr Arg Trp Met Lys His Glu Pro Gly Leu Gly
305                 310                 315                 320 agc tat ggc gac gag ctg ggc cgg gag cgc ggc tcc ccc agc gag cgc     1008
Ser Tyr Gly Asp Glu Leu Gly Arg Glu Arg Gly Ser Pro Ser Glu Arg
                325                 330                 335 tgc gaa gag cgt ggt ggg gac gcg gcc gtc tcg ccc ggg ggg ccc ccg     1056
Cys Glu Glu Arg Gly Gly Asp Ala Ala Val Ser Pro Gly Gly Pro Pro
                340                 345                 350 ctc ggc ctg gcg ccg ccg ccg cgc tac cct ggc agc ctg gac ggg ccc     1104
Leu Gly Leu Ala Pro Pro Pro Arg Tyr Pro Gly Ser Leu Asp Gly Pro
                355                 360                 365 ggc gcg ggc ggc gac ggc gac gac tac aag agc agc agc gag gag acc     1152
Gly Ala Gly Gly Asp Gly Asp Asp Tyr Lys Ser Ser Ser Glu Glu Thr
        370                 375                 380 ggt agc agc gag gac ccc agc ccg cct ggc ggc cac ctc gag ggc tac     1200
Gly Ser Ser Glu Asp Pro Ser Pro Pro Gly Gly His Leu Glu Gly Tyr
385                 390                 395                 400 cca tgc ccg cac ctg gcc tat ggc gag ccc gag agc ttc ggt gac aac     1248
Pro Cys Pro His Leu Ala Tyr Gly Glu Pro Glu Ser Phe Gly Asp Asn
                405                 410                 415 ctg tac gtg tgc att ccg tgc ggc aag ggc ttc ccc agc tct gag cag     1296
Leu Tyr Val Cys Ile Pro Cys Gly Lys Gly Phe Pro Ser Ser Glu Gln
                420                 425                 430 ctg aac gcg cac gtg gag gct cac gtg gag gag gag gaa gcg ctg tac     1344
Leu Asn Ala His Val Glu Ala His Val Glu Glu Glu Glu Ala Leu Tyr
        435                 440                 445 ggc agg gcc gag gcg gcc gaa gtg gcc gct ggg gcc gcc ggc cta ggg     1392
Gly Arg Ala Glu Ala Ala Glu Val Ala Ala Gly Ala Ala Gly Leu Gly
450                 455                 460 ccc cct ttt gga ggc ggc ggg gac aag gtc gcc ggg gct ccg ggt ggc     1440
Pro Pro Phe Gly Gly Gly Gly Asp Lys Val Ala Gly Ala Pro Gly Gly
465                 470                 475                 480 ctg gga gag ctg ctg cgg ccc tac cgc tgc gcg tcg tgc gac aag agc     1488
Leu Gly Glu Leu Leu Arg Pro Tyr Arg Cys Ala Ser Cys Asp Lys Ser
                485                 490                 495 tac aag gac ccg gcc acg ctg cgg cag cac gag aag acg cac tgg ctg     1536
Tyr Lys Asp Pro Ala Thr Leu Arg Gln His Glu Lys Thr His Trp Leu
                500                 505                 510 acc cgg ccc tac cca tgc acc atc tgc ggg aag aag ttc acg cag cgt     1584
Thr Arg Pro Tyr Pro Cys Thr Ile Cys Gly Lys Lys Phe Thr Gln Arg
        515                 520                 525 ggg acc atg acg cgc cac atg cgc agc cac ctg ggc ctc aag ccc ttc     1632
Gly Thr Met Thr Arg His Met Arg Ser His Leu Gly Leu Lys Pro Phe
        530                 535                 540 gcg tgc gac gcg tgc ggc atg cgg ttc acg cgc cag tac cgc ctc acg     1680
Ala Cys Asp Ala Cys Gly Met Arg Phe Thr Arg Gln Tyr Arg Leu Thr
545                 550                 555                 560 gag cac atg cgc atc cac tcg ggc gag aag ccc tac gag tgc cag gtg     1728
Glu His Met Arg Ile His Ser Gly Glu Lys Pro Tyr Glu Cys Gln Val
```

```
                     565                 570                 575
tgc ggc ggc aag ttc gca cag caa cgc aac ctc atc agc cac atg aag       1776
Cys Gly Gly Lys Phe Ala Gln Gln Arg Asn Leu Ile Ser His Met Lys
                580                 585                 590 atg cac gcc gtg ggg ggc gcg gcc ggc gcg gcc ggg gcg ctg gcg ggc       1824
Met His Ala Val Gly Gly Ala Ala Gly Ala Ala Gly Ala Leu Ala Gly
                595                 600                 605 ttg ggg ggc ctc ccc ggc gtc ccc ggc ccc gac ggc aag ggc aag ctc       1872
Leu Gly Gly Leu Pro Gly Val Pro Gly Pro Asp Gly Lys Gly Lys Leu
            610                 615                 620 gac ttc ccc gag ggc gtc ttt gct gtg gct cgc ctc acg gcc gag cag       1920
Asp Phe Pro Glu Gly Val Phe Ala Val Ala Arg Leu Thr Ala Glu Gln
625                 630                 635                 640 ctg agc ctg aag cag cag gac aag gcg gcc gcg gcc gag ctg ctg gcg       1968
Leu Ser Leu Lys Gln Gln Asp Lys Ala Ala Ala Ala Glu Leu Leu Ala
                645                 650                 655 cag acc acg cac ttc ctg cac gac ccc aag gtg gcg ctg gag agc ctc       2016
Gln Thr Thr His Phe Leu His Asp Pro Lys Val Ala Leu Glu Ser Leu
                660                 665                 670 tac ccg ctg gcc aag ttc acg gcc gag ctg ggc ctc agc ccc gac aag       2064
Tyr Pro Leu Ala Lys Phe Thr Ala Glu Leu Gly Leu Ser Pro Asp Lys
                675                 680                 685 gcg gcc gag gtg ctg agc cag ggc gct cac ctg gcg gcc ggg ccc gac       2112
Ala Ala Glu Val Leu Ser Gln Gly Ala His Leu Ala Ala Gly Pro Asp
            690                 695                 700 ggc cgg acc atc gac cgt ttc tct ccc acc tag                           2145
Gly Arg Thr Ile Asp Arg Phe Ser Pro Thr
705                 710
```

<210> SEQ ID NO 15
<211> LENGTH: 18
<212> TYPE: DNA
<213> ORGANISM: Homo sapiens
<220> FEATURE:
<221> NAME/KEY: Artificial sequence
<222> LOCATION: (1)..(18)
<223> OTHER INFORMATION: forward primer for L025 gene

<400> SEQUENCE: 15
tatctagcaa tggaccgt                                                   18

<210> SEQ ID NO 16
<211> LENGTH: 19
<212> TYPE: DNA
<213> ORGANISM: Homo sapiens
<220> FEATURE:
<221> NAME/KEY: Artificial sequence
<222> LOCATION: (1)..(19)
<223> OTHER INFORMATION: Reserse primer for L025 gene

<400> SEQUENCE: 16
ccgaaggtag tagcatgga                                                  19

<210> SEQ ID NO 17
<211> LENGTH: 21
<212> TYPE: DNA
<213> ORGANISM: Vaccinia virus
<220> FEATURE:
<221> NAME/KEY: Artificial sequence
<222> LOCATION: (1)..(21)
<223> OTHER INFORMATION: Forward primer for A46R and A47L genes

<400> SEQUENCE: 17
ttggctatta aacagtatgg a                                               21

```
<210> SEQ ID NO 18
<211> LENGTH: 18
<212> TYPE: DNA
<213> ORGANISM: Vaccinia virus
<220> FEATURE:
<221> NAME/KEY: Artificial sequence
<222> LOCATION: (1)..(18)
<223> OTHER INFORMATION: Reserse primer for A46R and A47L genes

<400> SEQUENCE: 18
ggatcccgat aacaaatg                                                  18

<210> SEQ ID NO 19
<211> LENGTH: 25
<212> TYPE: DNA
<213> ORGANISM: Vaccinia virus
<220> FEATURE:
<221> NAME/KEY: Artificial sequence
<222> LOCATION: (1)..(25)
<223> OTHER INFORMATION: Forward primer for mB5R

<400> SEQUENCE: 19
atgaaaacga tttccgttgt tacgt                                          25

<210> SEQ ID NO 20
<211> LENGTH: 24
<212> TYPE: DNA
<213> ORGANISM: Vaccinia virus
<220> FEATURE:
<221> NAME/KEY: Artificial sequence
<222> LOCATION: (1)..(24)
<223> OTHER INFORMATION: Reserse primer for mB5R

<400> SEQUENCE: 20
tcacggtagc aatttatgga actt                                           24

<210> SEQ ID NO 21
<211> LENGTH: 25
<212> TYPE: DNA
<213> ORGANISM: Vaccinia virus
<220> FEATURE:
<221> NAME/KEY: Artificial sequence
<222> LOCATION: (1)..(25)
<223> OTHER INFORMATION: Forward primer for sB5R

<400> SEQUENCE: 21
atgaaaacga tttccgttgt tacgt                                          25

<210> SEQ ID NO 22
<211> LENGTH: 24
<212> TYPE: DNA
<213> ORGANISM: Vaccinia virus
<220> FEATURE:
<221> NAME/KEY: Artificial sequence
<222> LOCATION: (1)..(24)
<223> OTHER INFORMATION: Reserse primer for sB5R

<400> SEQUENCE: 22
tcacggtagc aatttatgga actt                                           24

<210> SEQ ID NO 23
<211> LENGTH: 20
<212> TYPE: DNA
<213> ORGANISM: Vaccinia virus
<220> FEATURE:
<221> NAME/KEY: Artificial sequence
<222> LOCATION: (1)..(20)
```

```
<223> OTHER INFORMATION: Forward primer for TK gene

<400> SEQUENCE: 23
gttatagtag ccgcactcga                                              20

<210> SEQ ID NO 24
<211> LENGTH: 21
<212> TYPE: DNA
<213> ORGANISM: Vaccinia virus
<220> FEATURE:
<221> NAME/KEY: Artificial sequence
<222> LOCATION: (1)..(21)
<223> OTHER INFORMATION: Reserse primer for TK gene

<400> SEQUENCE: 24
atttcagctg aatatgaagg a                                            21

<210> SEQ ID NO 25
<211> LENGTH: 20
<212> TYPE: DNA
<213> ORGANISM: Homo sapiens
<220> FEATURE:
<221> NAME/KEY: Artificial sequence
<222> LOCATION: (1)..(20)
<223> OTHER INFORMATION: Forward primer for PD1 antibody gene

<400> SEQUENCE: 25
tcataaatac ccgagccacc                                              20

<210> SEQ ID NO 26
<211> LENGTH: 20
<212> TYPE: DNA
<213> ORGANISM: Homo sapiens
<220> FEATURE:
<221> NAME/KEY: Artificial sequence
<222> LOCATION: (1)..(20)
<223> OTHER INFORMATION: Reserse primer for PD1 antibody gene

<400> SEQUENCE: 26
acccattcaa gacccttttcc                                             20

<210> SEQ ID NO 27
<211> LENGTH: 18
<212> TYPE: DNA
<213> ORGANISM: Vaccinia virus
<220> FEATURE:
<221> NAME/KEY: Artificial sequence
<222> LOCATION: (1)..(18)
<223> OTHER INFORMATION: Forward primer for control gene

<400> SEQUENCE: 27
tgttgttcgc tgctatga                                                18

<210> SEQ ID NO 28
<211> LENGTH: 20
<212> TYPE: DNA
<213> ORGANISM: Vaccinia virus
<220> FEATURE:
<221> NAME/KEY: Artificial sequence
<222> LOCATION: (1)..(20)
<223> OTHER INFORMATION: Reserse primer for control gene

<400> SEQUENCE: 28
tggcacaacc atatcttgta                                              20
```